US012059506B2

(12) United States Patent
Morra et al.

(10) Patent No.: US 12,059,506 B2
(45) Date of Patent: Aug. 13, 2024

(54) COATED IMPLANTABLE DEVICE

(71) Applicant: NOBIL BIO RICERCHE S.R.L., Brescia (IT)

(72) Inventors: Marco Morra, Brescia (IT); Clara Cassinelli, Brescia (IT); Giorgio Iviglia, Brescia (IT); Elisa Torre, Brescia (IT)

(73) Assignee: NOBIL BIO RICERCHE S.R.L., Brescia (IT)

( * ) Notice: Subject to any disclaimer, the term of this patent is extended or adjusted under 35 U.S.C. 154(b) by 433 days.

(21) Appl. No.: 16/631,393

(22) PCT Filed: Jul. 2, 2018

(86) PCT No.: PCT/IB2018/054893
§ 371 (c)(1),
(2) Date: Jan. 15, 2020

(87) PCT Pub. No.: WO2019/016634
PCT Pub. Date: Jan. 24, 2019

(65) Prior Publication Data
US 2020/0215225 A1 Jul. 9, 2020

(30) Foreign Application Priority Data

Jul. 18, 2017 (IT) .................. 102017000081175

(51) Int. Cl.
| | | |
|---|---|---|
| A61L 27/58 | (2006.01) | |
| A61K 31/192 | (2006.01) | |
| A61K 31/352 | (2006.01) | |
| A61K 31/7048 | (2006.01) | |
| A61K 36/87 | (2006.01) | |
| A61L 27/02 | (2006.01) | |
| A61L 27/06 | (2006.01) | |
| A61L 27/12 | (2006.01) | |
| A61L 27/32 | (2006.01) | |
| A61L 27/34 | (2006.01) | |
| A61L 27/36 | (2006.01) | |
| A61L 27/54 | (2006.01) | |
| A61L 27/56 | (2006.01) | |
| B33Y 70/10 | (2020.01) | |
| B33Y 80/00 | (2015.01) | |
| C08L 5/08 | (2006.01) | |

(52) U.S. Cl.
CPC ............ *A61L 27/06* (2013.01); *A61K 31/192* (2013.01); *A61K 31/352* (2013.01); *A61K 31/7048* (2013.01); *A61K 36/87* (2013.01); *A61L 27/34* (2013.01); *A61L 27/3637* (2013.01); *A61L 27/365* (2013.01); *A61L 27/54* (2013.01); *C08L 5/08* (2013.01); *A61K 2236/333* (2013.01); *A61K 2236/53* (2013.01); *A61L 2300/216* (2013.01); *A61L 2300/61* (2013.01); *A61L 2400/18* (2013.01); *A61L 2420/06* (2013.01); *A61L 2420/08* (2013.01); *A61L 2430/02* (2013.01)

(58) Field of Classification Search
CPC ...... A61L 27/06; A61L 27/34; A61L 27/3637; A61L 27/365; A61L 27/54; A61L 2300/216; A61L 2300/61; A61L 2400/18; A61L 2420/06; A61L 2420/08; A61L 2430/02; A61L 27/28; A61K 31/192; A61K 31/352; A61K 31/7048; A61K 36/87; A61K 2236/333; A61K 2236/53; C08L 5/08
See application file for complete search history.

(56) References Cited

U.S. PATENT DOCUMENTS

| | | | | |
|---|---|---|---|---|
| 8,172,844 B2 * | 5/2012 | Gazza | ..................... | A61L 27/34 606/76 |
| 2003/0180395 A1 * | 9/2003 | Bueter | .................... | A61P 23/00 424/725 |
| 2005/0048121 A1 * | 3/2005 | East | ........................ | A61L 27/54 528/274 |

FOREIGN PATENT DOCUMENTS

| | | | | |
|---|---|---|---|---|
| EP | 2560694 B1 * | 11/2014 | ............. | A61L 27/20 |
| WO | 2006/038056 A1 | 4/2006 | | |
| WO | 2008/144178 A1 | 11/2008 | | |
| WO | 2010/020972 A1 | 2/2010 | | |
| WO | 2014/169959 A1 | 10/2014 | | |
| WO | 2015/014872 A1 | 2/2015 | | |

OTHER PUBLICATIONS

Raskin, Ilya, and Christophe Ripoll. "Can an apple a day keep the doctor away?." Current pharmaceutical design 10.27 (2004): 3419-3429. (Year: 2004).*

(Continued)

Primary Examiner — Mina Haghighatian
Assistant Examiner — Janice Y Silverman
(74) Attorney, Agent, or Firm — Merchant & Gould P.C.

(57) ABSTRACT

Implant devices are coated with biologically active compounds, in particular with plant extracts from vinification residues. The implant devices are bone implants, and in particular dental implants. A method for functionalizing a surface of an implant device is includes the steps of a) optionally, treating the surface of the implant device with air, oxygen, argon, nitrogen plasma, and plasma capable of removing the surface layer of hydrocarbon contamination, b) treating the surface of the implant with an amine substrate, c) treating the surface of the implant resulting from step b), alternatively with a marcs extract, and drying the functionalized surface, or by co-adsorbing a marcs extract and hyaluronic acid, and drying the functionalized surface, or by adsorbing hyaluronic acid and post-adsorbing a marcs extract, and drying of the functionalized surface.

8 Claims, 19 Drawing Sheets

(56) References Cited

OTHER PUBLICATIONS

Revilla et al. Food Chemistry, vol. 61, No. 1/2, pp. 201-206, 1998. (Year: 1998).*
MacPhillamy, H.B., Drugs from Plants: Plant Science Bulletin, Apr. 1963, vol. 9, Issue 2 pp. 1-15. (Year: 1963).*
Park et al. Biomaterials 33 (2012) 5468- 5477. (Year: 2012).*
Liu et al. Biomacromolecules 2012, 13, 3611-3619. (Year: 2012).*
Tokareva et al. Chemistry of Heterocyclic Compounds 2017, 53(1), 21-35. (Year: 2017).*
Zhang et al. Applied Surface Science 287 (2013) 341-348. (Year: 2013).*
Di Lorenzo, Arianna, et al. "Effect of winemaking on the composition of red wine as a source of polyphenols for anti-infective biomaterials." Materials 9.5 (2016): 316. (Year: 2016).*
Cordoba, A. et al., "Favonoid-Modified Surfaces: Multifunctional Bioactive Biomaterials with Osteopromotive, Anti-Inflammatory, and Anti-Fibrotic Potential", Adv. Healthcare Mater., 4: 540-549 (2015).
Picart, C. et al., "Buildup Mechanism for Poly(L-lysine)/Hyaluronic Acid Films onto a Solid Surface", Langmuir, 17: 7414-7424 (2001).
Shi, J. et al., "Optimization of the extraction of polyphenols from grape seed meal by aqueous ethanol solution", Food, Agriculture & Environment, 1(2): 42-47 (2003).
International Search Report and Written Opinion of the International Searching Authority for International Patent Application No. PCT/IB2018/054893 mailed Nov. 19, 2018, 18 pages.

* cited by examiner

Potenziale = Potential

Titanio = Titanium

Potenziale = Potential

Titanio = Titanium

Potenziale = Potential

Estratti = Extracts

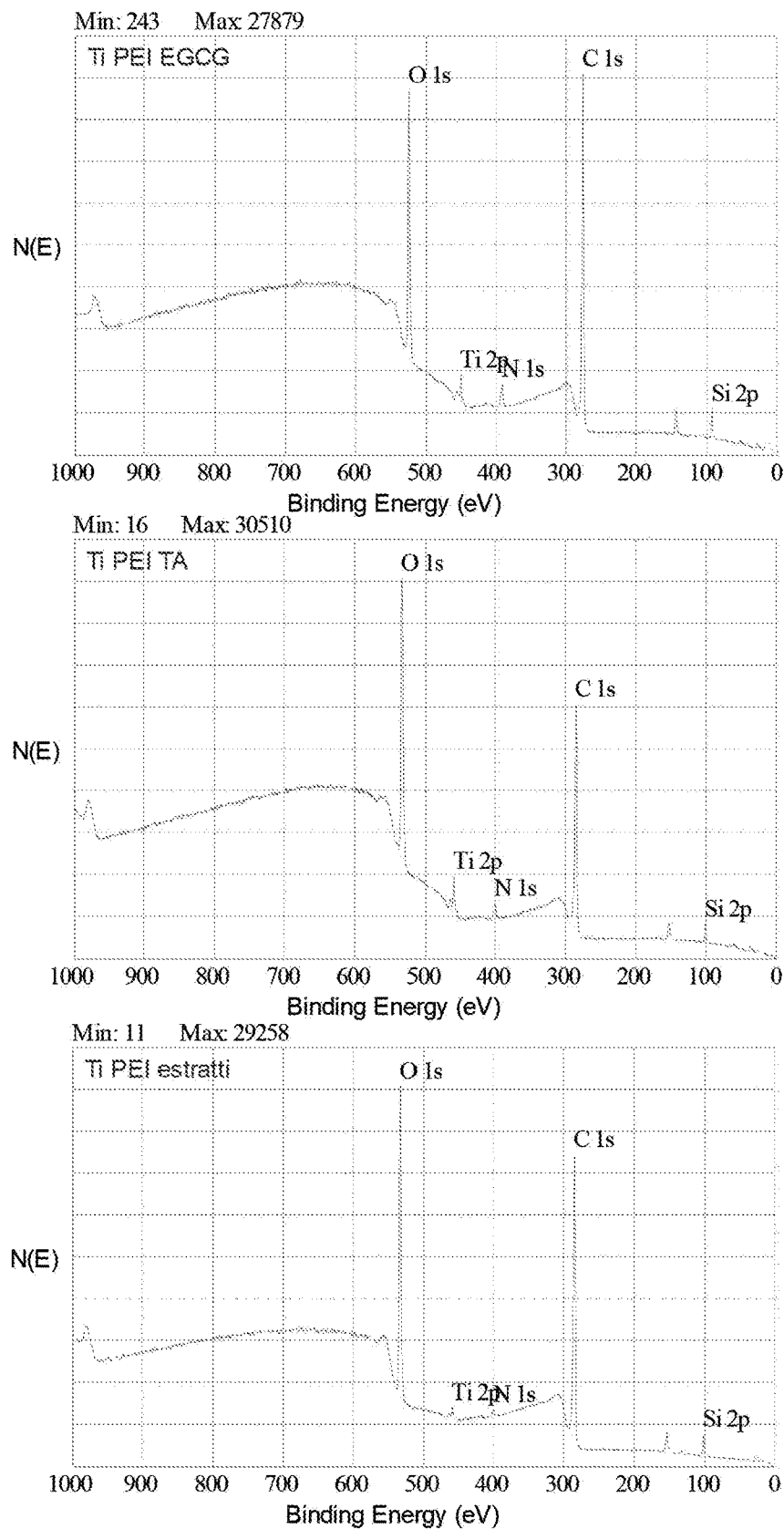
FIG. 4    Estratti = Extracts

Potenziale = Potential

Estratti = Extracts

Titanio = Titanium

Potenziale = Potential

Estratti = Extracts

Titanio = Titanium

Potenziale = Potential

Estratti = Extracts

Composti puri = Pure compounds

Potenziale = Potential

Estratti = Extracts

Estratti = Extracts

Estratti = Extracts

Potenziale = Potential

FIG. 22  Titanio = Titanium

% riduzione assorbanza = % absorbance reduction

Strato = Layers

Strati = Layers

% riduzione assorbanza = % absorbance reduction

Variazione % potere antiossidante = % antioxidant power variation

Solo estratti = Extracts alone

Estratti HA = HA extracts

COATED IMPLANTABLE DEVICE

CROSS-REFERENCE TO RELATED APPLICATIONS

This application is a National Stage Application of PCT/IB2018/054893, filed 2 Jul. 2018, which claims benefit of Patent Application Serial No. 102017000081175, filed 18 Jul. 2017 in Italy and which applications are incorporated herein by reference. To the extent appropriate, a claim of priority is made to each of the above-disclosed applications.

FIELD OF THE INVENTION

The present invention relates to implant devices coated with biologically active compounds, in particular with plant extracts from vinification residues. Implant devices are in particular bone implants, and more preferably dental implants.

BACKGROUND OF THE INVENTION

The insertion of an implant device into the human body necessarily involves a wound and the subsequent tissue repair process. Tissue repair, in nature, occurs by means of the natural mechanism of wound inflammation and healing. In the presence of an implantation device, the natural inflammation process may be altered, due to the chronic presence of what is perceived as a foreign body, giving rise to results detrimental to the functionality of the device itself and health. The inflammation and healing process is mediated by inflammatory cells, mainly neutrophils and macrophages. These cells reach the wound site and release molecules, called cytokines and chemokines, which recall other inflammatory cells and stimulate the activity thereof. In normal tissue repair, the cytokines and chemokines produced by the inflammatory cells appear in precise temporal sequences and concentrations, directing the healing process. Some of these molecules have pro-inflammatory effect, other anti-inflammatory effect. By appropriately balancing the pro-inflammatory stimuli required, for example, for the removal of damaged tissue, particulate matter, bacteria, and the anti-inflammatory ones required to keep the process under control and avoid excessive damage, the defense mechanisms of the organism normally manage to induce tissue repair.

In pathological situations, or in the presence of implant devices, the normal production of pro- and anti-inflammatory stimuli by the involved cells may be unbalanced: for example, particles of solid material (e.g. fragments of implant material), of size of the micron, which cannot be phagocytized by the inflammatory cells responsible for their elimination, stimulate the inflammatory cells themselves (macrophages). Under the influence of a foreign body (the particle) which fails to phagocytate, the macrophage emits further pro-inflammatory chemokines and cytokines, to recall other inflammatory cells in the site to eliminate the foreign stimulus. If the stimulus remains (the non-phagocytotic foreign material), the process continues to repeat itself, giving rise to situations of chronic inflammation which can be a major source of problems, for example for orthopedic devices.

In other cases, the unbalanced production of chemokines and cytokines can induce transformations and alterations in cells which do not allow complete healing and lead to the formation of abnormal tissue. The typical case is the formation of restenotic tissue secondary to the introduction of coronary or peripheral stents.

In this context, it should be underlined that even if in the common language the word "inflammation" has generally negative connotation, the "acute" inflammation, secondary to a wound, identified by swelling, pain, redness and heat, is actually the natural process required for wound healing itself. The inflammatory activity presides over the removal from the damaged tissue of any bacteria and sets in motion the repair mechanisms. Inflammation cannot and should not be suppressed, otherwise there would be no healing, but it must be controlled in order to obtain the desired osseointegration of the implant.

The material normally used for bone implants is titanium, which is characterized by an advantageous bio-inertia which promotes the natural tissue protection. However, it is desirable—and already partially implemented—to coat the implant surface with bioactive material which can effectively act on the osseointegration process. A typical material used for this purpose is hyaluronic acid.

It is also known to use anti-inflammatory molecules, in particular molecules belonging to the flavonoid class, for the coating of bone implants in order to induce a better osseointegration. Cordoba et al. (Flavonoid-Modified Surfaces: Multifunctional Bioactive Biomaterials with Osteopromotive, Anti-Inflammatory, and Anti-Fibrotic Potential, *Adv. Healthcare Mater.* 2015, 4, 540-549) describe the immobilization of taxifolin or quercitrin on titanium surfaces by covalent bonds and suggest their application to bone implants or coronary stents and WO 2014/169959 describes bone implants on which flavonoid molecules selected from quercitrin, taxifolin, galangine, diosmethine and chrysin are immobilized, by binding with an aminosilane.

One problem we have found in coating titanium implants with antioxidant molecules such as those identified above is the fact that it is not easy to achieve a complete overcoat of the implant surface. We have also found that the degree of coating of the implant surface affects the osteonductive action of the device and is therefore a desirable target.

SUMMARY OF THE INVENTION

The above problem has been solved according to the invention by coating the implant surface with a vegetable extract deriving from marcs.

Therefore, the present invention relates to an implant device comprising a surface coating obtained from plant extracts of marcs.

Secondly, the present invention relates to a process for extracting marcs and functionalizing the surface of an implant device with the extract thus obtained.

These and other objects form the subject of the appended claims, the definitions of which are an integral part of the present description.

The term "marcs" refers to the waste of the vinification process, in particular grape seeds and peels. As process waste, the raw material does not present substantial costs. It is known in the art that polyphenols in complex mixture can be easily and cost-effectively extracted from waste of this nature, for example with the use of hydroalcoholic solutions (John Shi, Jianmei Yu, Joseph Pohorly, J. Christopher Young, Mike Bryan, Ying Wu, Optimization of the extraction of polyphenols from grape seed meal by aqueous ethanol solution, Food, Agriculture & Environment Vol.

1(2): 42-47. 2003), but these extracts are not used as they are for local use, as they are water-soluble and not very stable.

BRIEF DESCRIPTION OF THE FIGURES

FIG. 4 shows the XPS spectra of the functionalized titanium samples: Ti+PEI+EPGCG, Ti+PEI+tannic acid and Ti+PEI+extracts from marcs;

DESCRIPTION OF THE INVENTION

Figure 1:
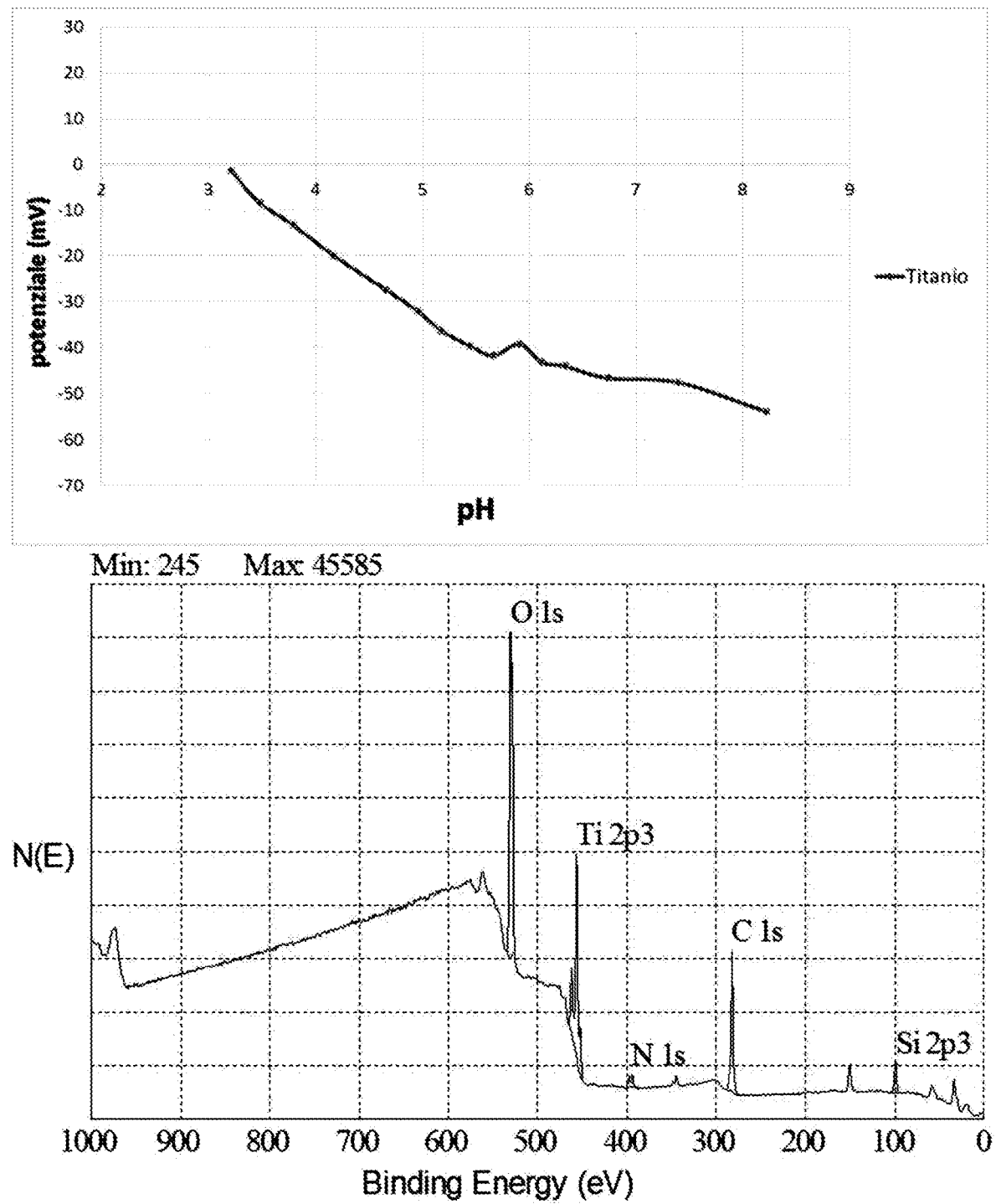
FIG. 1 shows a graph of theta potential as a function of pH and an XPS spectrum of a Titanium sample.

The present invention is inspired by our observation that the extracts from vinification residues are an excellent material for surface modification processes aimed at immobilizing biological molecules of plant origin, in particular polyphenols, on the surface of an implant device. In particular, the interaction between a molecularly complex polyphenol mixture, in terms of size, charge and solution properties and a surface with a high density of basic sites (amine groups) allows the implementation of a homogeneously functionalized and complete surface layer. This result is not obtained starting, as suggested in the prior art, from flavonoids or other pure polyphenols.

Without being bound to any theory, we believe that the high charge density of the device surface functionalized with amino groups and the molecular complexity of the species present in the extracts cooperate so that the same surface selects the species with greater affinity from the polyphenolic solution and optimizes the space encumbrance in order to create a functionally homogeneous surface layer. The features of this surface layer exhibit advantages for some applications, in particular they exert a favorable influence on cell growth. The process therefore finds advantageous application in the surface modification of materials which owe their function to an effective interaction with cells, in particular implant devices, more particularly bone implants, even more particularly titanium dental implant screws.

Therefore, the invention first relates to a process for the surface functionalization of an implant device comprising, in this order, the steps of:

a) optionally, treating the surface of the implant device with air, oxygen, argon, nitrogen plasma, or generally plasma capable of removing the surface layer of hydrocarbon contamination;

b) treating the surface of the implant with an amine substrate;

c) treating the surface of the implant resulting from step b) with a marcs extract and drying said functionalized surface.

In a different embodiment, the process for the surface functionalization of an implant device comprises, in order, the steps of:

a) optionally, treating the surface of the implant device with air, oxygen, argon, nitrogen plasma, or generally plasma capable of removing the surface layer of hydrocarbon contamination;

b) treating the surface of the implant with an amine substrate;

c) treating the surface of the implant resulting from step b) by co-adsorption of a marcs extract and hyaluronic acid or adsorption of hyaluronic acid and post-adsorption of a marcs extract and drying said functionalized surface.

The implant device is any device intended to come into contact for a prolonged time with the human or animal body and may for example be selected from cardiovascular stents or bone implants of various types. In particular, the device according to the invention is a titanium bone implant, more preferably a titanium dental implant screw.

Step a) has the advantage of facilitating the adhesion of the amine substrate on the surface of the device.

In step b), the amine substrate is preferably polyethyleneimine. Preferably, an aqueous solution of amine substrate, more preferably of polyethyleneimine, with a concentration between 0.03 and 0.15% by volume, preferably between 0.05 and 0.1% by volume, will preferably be used. The implant device is treated, preferably immersed in said solution of amine substrate for more than 1 hour, preferably about 2 hours, and preferably at room temperature. The use of the amine substrate has proved to be very advantageous with respect to the known functionalization of the prior art, which provides for the use of silanes from solutions in toluene or the like and in anhydrous conditions.

Step c) may be carried out, for example, by simply immersing the implant in a solution or suspension-solution of the marcs extract obtained as described hereinafter. The treatment is preferably carried out at a temperature between 15° C. and 30° C. or at room temperature and for more than 4 hours, more preferably more than 6 hours, even more preferably between 10 and 14 hours.

When in step c) hyaluronic acid is used, it is used in aqueous solution having a concentration preferably comprised between 0.01% and 0.15% by weight/volume, or between 0.01% and 0.1% by weight/volume.

In certain embodiments, the process of the invention comprises a repetition of steps b) and c), in the order, from 2 to 8 times, preferably from 3 to 6 times, so as to create a multilayer coating of polyphenolic molecules deriving from said marcs extracts. If the process comprises a co-adsorption or post-adsorption of marcs extracts after adsorption of hyaluronic acid as defined above:

- according to a first variant, an aqueous solution of hyaluronic acid with a concentration of between 0.05% and 0.15% by weight/volume will be used, and the outermost layer of the coating will be obtained by adsorption of the marcs extracts alone;
- according to a second variant, an aqueous solution of hyaluronic acid with a concentration lower than 0.02% by weight/volume will be used, and all the layers of the coating will comprise hyaluronic acid.

In certain embodiments, the process of the invention comprises a sterilization step by means of gamma rays at 25 kGy of the implant treated according to step c).

The marcs extract can derive from the marcs of grapes of various origins or from mixtures thereof. For example, marcs of vines of white grapes or red grapes or mixtures thereof may be used.

In certain embodiments, the marcs will derive from grapes with a high content of anthocyanins.

In certain embodiments, the marcs will be selected from "nebbiolo" vine marcs, "barbera" vine, "croatina" vine, "arneis" vine and mixtures thereof. More preferably, "croatina" vine marcs will be used.

It is also possible to use mixtures of extracts deriving from the extraction of single-grape marcs instead of mixing the marcs of the various single-grape varieties before the extraction step. This embodiment allows to carry out the extraction in the vicinity of the production sites of the various wines, limiting the subsequent transport operations to the production site of the implant devices to the extracts alone, instead of the totality of the marcs.

The method of preparing a vegetable extract from marcs form a second object of the invention. Such a method comprises the steps of:
i) drying the marcs,
ii) milling the dried marcs,
iii) washing the dried and milled marcs with water at acidic pH,
iv) extracting the marcs obtained from step iii) with an aqueous solution and an organic solvent which can be mixed with water,
v) centrifuging the mixture of step iv), separating the liquid phase and removing the organic solvent, thereby obtaining a marcs extract solution/suspension,
vi) preferably, separating the suspended phase, thereby obtaining an extract in solution.

The step i) of drying the marcs is preferably carried out at a temperature between 30° C. and 50° C., more preferably between 37° C. and 43° C. and preferably for more than 24 hours, more preferably higher than 48 hours. In this step, a ventilated stove may be used, for example.

The washing step iii) is carried out with water at a pH preferably comprised between 2 and 6.5, more preferably 3-5.5.

The extraction step iv) is preferably carried out with a mixture of water and acetone, preferably in water/organic solvent ratio between 40/60 and 60/40, more preferably between 45/55 and 55/45 and preferably using a water+ organic solvent/marcs (deriving from step iii) mixture ratio comprised between 5:1 and 7:1 mL/g, more preferably 6:1 mL/g. The step iv) is preferably carried out at a temperature ranging from 20° ° C. to 40° C. and at a pH ranging from 5 to about 7, depending on the type of marcs used. In particular, it was observed that the vines of red wines (Ovello, barbera, croatina) have a pH between 5 and 6.5, the white vines (arneis) have a pH of about 7.

Step v) is preferably carried out by centrifugation in the range of 5000 to 7000 rpm. The elimination of the organic solvent, in the case of low-boiling solvent (e.g. acetone), can be carried out for example by means of a rotavapor.

The step vi) is optional but preferable and may be carried out by decanting the suspension and then separating the phase in solution by centrifugation, preferably operating between 5000 and 7000 rpm. Alternatively, filtration may be carried out, possibly adding a flocculant to the suspension. The advantage of separating the suspended phase from that in solution is that only the molecules present in the solution are capable of binding to the amine substrate which coats the implant device, while the suspended particles may accumulate on the outer surface, making such a surface inhomogeneous. The solution phase contains only water-soluble polyphenols or other water-soluble molecules. The solution phase does not contain, for example, quercitrin, as this molecule is insoluble in the aqueous phase.

The extract obtained by the above method, in particular the phase in solution of said extract, comprises gallic acid, quercetin, rutin and malvidin-3-glucoside.

A third object of the invention relates to an implant device as defined above, preferably a titanium bone implant, more preferably a titanium dental implant screw, comprising a surface functionalization with one or more layers of amine substrate alternating with one or more layers of polyphenols extracted from marcs, wherein the layer adhered to the implant surface consists of the amine substrate and wherein the one or more layers of said polyphenols produce a degree of surface coating greater than 90%, preferably greater than 95%, more preferably greater 98%, even more preferably more than 99%.

The degree of coating of an implant device can be calculated as follows:
1) calculate the average percentage values of titanium (Ti % mean) measured by XPS analysis of at least two standard implant samples coated with polyethyleneimine;

2) measure the percentage value of titanium (Ti % sample) of the implant device under examination;
3) calculate the degree of coating according to the formula:

coating %=100−(Ti % sample×100)/Ti % mean.

The XPS analysis method is defined in the following description.

In preferred embodiments, the one or more layers of said polyphenols of the implant device as defined above have a homogeneously acidic functionality, characterized by a single defined pKa value.

In certain embodiments, the polyphenols extracted from the marcs of said one or more layers of polyphenols comprise gallic acid, quercetin, rutin and malvidin-3-glucoside.

In certain embodiments, the polyphenols extracted from the marcs of said one or more layers of polyphenols comprise anthocyanins.

The implant device of the invention may be obtained by means of the marcs functionalization and extraction process described above. It should be noted that, given the complexity of the composition of compounds contained in a plant extract as described above, it is not possible to define exactly all the molecules which can be adsorbed on the implant surface, except by the method adopted for its preparation.

Preferably, the implant device of the invention comprises from 2 to 8 layers, more preferably from 3 to 6 layers, of amine substrate and from 2 to 8 layers, more preferably from 3 to 6 layers, of polyphenols from said marcs extracts, arranged alternately as defined above.

In certain embodiments, the implant device comprises a surface functionalization with one or more layers of amine substrate alternating with one or more layers comprising polyphenols extracted from marcs and hyaluronic acid, wherein the layer adhered to the implant surface consists of the amine substrate. Preferably, the outermost layer consists of polyphenols from marcs extracts alone.

The marcs extracts are those described above. Preferably, the implant device of the invention comprises polyphenols obtained from marcs extracts selected from marcs of "nebbiolo" vine, "barbera" vine, "croatina" vine, "arneis" vine or mixtures thereof, or more preferably marcs from "croatina" vine.

In a preferred embodiment, the amine substrate is a polyethyleneimine. The polyethyleneimine may be linear or branched, preferably branched, and has a molecular weight of more than 10,000 Da.

Experimental Part

Definition and Identification of the Extracts

The initial experiments were carried out starting from marcs of Nebbiolo da Barbaresco grapes, cru Ovello. The extraction process first involves drying the marcs at a temperature of about 40° C., for 48 hours in a ventilated oven. The peels and seeds thus deprived of water are ground and reduced to powder to increase the surface area and therefore the yield in the extraction of polyphenols. The "flour" then undergoes three process steps:
   washing with acidified water to remove large impurities, bacteria and any fungus on the skins;
   extraction with water:acetone 50:50 solution in relation to the vegetable mass of 1 g of marcs per 6 ml of solution;
   centrifugation of the extract, sampling of the solution rich in polyphenols and concentration in rotavapor to eliminate the organic part of the solvent (acetone).

At the end of the process, the extract rich in polyphenols is then in the form of aqueous solution/suspension. With time and to a large extent as a function of the specific vine, there is a process of precipitation of part of the suspended material.

The characterization of the extract was performed by spectrophotometric and chromatographic techniques.

In particular, the main parameter used to define the extracts is the total amount of polyphenols, expressed as Gallic Acid Equivalent (GAE) in mg/mL. This parameter is evaluated by means of the Folin-Ciocalteau test (FC test), which produces an absorbance value referred to a calibration line made with gallic acid, a compound taken as reference by convention. In comparison tests with pure compounds, the latter are used in concentrations such as to provide the same GAE value with respect to the extracts. In addition to the FC test, the extracts are characterized by their antioxidant power through the DPPH test and the amount of anthocyanins (using malvidin-3-glucoside as a reference). Finally, the main polyphenolic molecules were qualitatively and quantitatively analyzed using liquid chromatography.

Total Polyphenol Content (FC Test)

The Folin-Ciocalteau test allows, by using a reagent (the Folin-Ciocalteau reagent), the quantification of the total polyphenol content within the analysis solution, since the total polyphenols, in an alkaline environment, reduce the mixture of phototungstic acid and phosphomolybdic acid, constituting the Folin—Ciocalteau reagent, in a mixture of tungsten and molybdenum oxides having a blue color. Going then to analyze the absorbance (i.e. the intensity of the blue color) by means of a UV/Vis spectrophotometer at the wavelength of 765 nm, the solution in which a suitable amount of reagent is inserted, we can quantify the polyphenolic content of the solution, expressed as mg/mL of gallic acid equivalents.

Antioxidant Power (DPPH Test)

The DPPH test allows to determine the antioxidant power by reacting the sample to be analyzed with a solution of DPPH (2,2-diphenyl-1-picrylhydrazyl). The antioxidant compounds are capable of transferring a hydrogen atom to the radical, causing a discoloration of the solution. The decrease of the peak at 525 nm of the DPPH radical is then analyzed with UV-Vis spectrometry after a predetermined incubation time. This discoloration is proportional to the antioxidant charge present in the sample.

Quantification of Anthocyanins (Ribereau-Goyon and Stonestreet Method)

This method is based on the process of discoloration of the anthocyanins which occurs by means of bisulfite.

Polyphenolic Spectrum Analysis by Liquid Chromatography (HPLC)

In order to compare the results obtained by means of what is present in the literature, an analysis method already used by Wittenaur et al. was implemented.

The method used for the analysis involves the use of two mobile phases:
   Mobile phase A (MP A): 2% acetic acid in water;
   Mobile phase B (MP B): 0.5% Acetic acid in 50:50 Water:Acetonitrile.

The developed method foresees a gradient as reported in the following table 1:

| Time [min] | MP A | MP B |
|---|---|---|
| 0-35 | 100 → 95 | 0 → 5 |
| 35-80 | 95 → 80 | 5 → 20 |

-continued

| Time [min] | MP A | MP B |
|---|---|---|
| 80-110 | 80 → 0 | 20 → 100 |
| 110-113 | 0 | 100 |
| 113-123 | 0 → 100 | 100 → 0 |

The parameters used were the following:
Luna C8 column
Flow 0.8 ml/min
Injection volume 20 µl
Temperature 25° C.

By using an HPLC instrument coupled to a "diode array", it is possible to obtain the spectrum of the polyphenolic molecules which make up the extracts; the following molecules were quantified, based on the calibration lines made with the standards: gallic acid, quercetin, rutin and malvidin-3-glucoside.

The characterization according to the indicated methods of our starting extract gave the results shown in the following table 2:

| DPPH [%] | FC [mg/ml GAE] | Total anthocyanins [mg/l] | Gallic add [mg/l] | Quercetin [mg/l] | Rutin [mg/l] | Malvidin-3-glucoside [mg/l] |
|---|---|---|---|---|---|---|
| 44.33 | 3.44 | 74.4 | 19.43 | 66.46 | 38.45 | 3.76 |

Procedure for the Functionalization of an Implant Device

For surface functionalization tests, the solution phase of the extract was diluted to reach an FC value of about 2 (value according to the FC test). All comparative experiments with pure compounds were made starting from solutions thereof with the same FC value.

The process involves the functionalization of the material to be covered by adsorption of polyethyleneimine (PEI) from aqueous solution in concentration in the range 0.05-0.1% (volume), at room temperature and for a time of 2 hours. The material on which the adsorption process must take place is preferentially pretreated with a plasma of air, oxygen or argon to favor the interaction between surface and polycationic chain of PEI. After the functionalization has been carried out, the washing is carried out and the material is put into contact with the aqueous solution of the extracts overnight at room temperature. The material is then washed. Analytical evidence is acquired by:

Measuring the ϑ Potential (Theta Potential).

This parameter is an indirect measure of the surface charge and therefore of the chemical groups possibly present on a surface and is obtained by flowing an aqueous solution of known and constant ionic strength in the capillary channel consisting of two identical surfaces of the material to be evaluated, housed in the appropriate cell and measuring the current which develops as a result of the transfer of charges (streaming current). The measurement is carried out as a function of pH.

The experimental method is therefore the following: for each experiment, two titanium sheets of dimensions 2×1 cm are made, cutting them out from a 0.25 mm thick titanium sheet (Titanium, Sigma Aldrich, code 267503-25.2G). The sheets are subjected to the various functionalization processes (adsorption of polyethyleneimine, extracts, pure compounds) and placed in the measuring cell of Surpass 3, a ϑ potential meter produced by the Anton Paar company. The tests are performed by measuring the streaming current in the pH range 8-2, in 1 mM solution of KCl. All parameters are controlled by the instrument software.

XPS (X-Ray Photoelectron Spectroscopy) Analysis.

Using this technique, we obtain the qualitative and quantitative chemical composition of the first nanometers of thickness of the surface of a material.

The experimental method is the following: samples obtained as in the case above, but of dimensions 1×1 cm, are analyzed by means of an XPS Perkin Elmer PHI 5600 ESCA System spectrophotometer. It is provided with a monochromatic X-ray source with an Al anode, maintained at 10 kV with a power of 200 W. The depth analyzed is about 5 nm. The pressure inside the analysis chamber was kept at about $10^{-9}$ Torr. The result of the analysis is expressed in "atomic %", using the instrument software and the sensitivity factors provided by the manufacturer.

The results obtained are discussed below.

Starting from the evaluation of titanium as material to be modified on the surface by the present process, FIG. 1 shows, at the top, the ϑ potential measured as a function of pH and the XPS spectrum at the bottom. The ϑ potential is very negative (−54 mV) at the basic end of the measurement and tends uniformly towards lower absolute values as the pH decreases. This behavior indicates that the potential value is substantially determined by the adsorption at the interface of the ionic species most present in solution, in particular hydroxyls at an alkaline pH, gradually balanced by hydrogen ions. The trend is that expected for materials which do not have specific acid-base functionality on the surface and in which the potential is governed by ions in solution. The XPS spectrum instead shows the presence on the surface of the constitutive elements Ti, O (on the surface, titanium is oxidized by contact with the atmosphere), inevitably adsorbed carbon and the common contaminants N and Si, present in small quantities.

Figure 2:
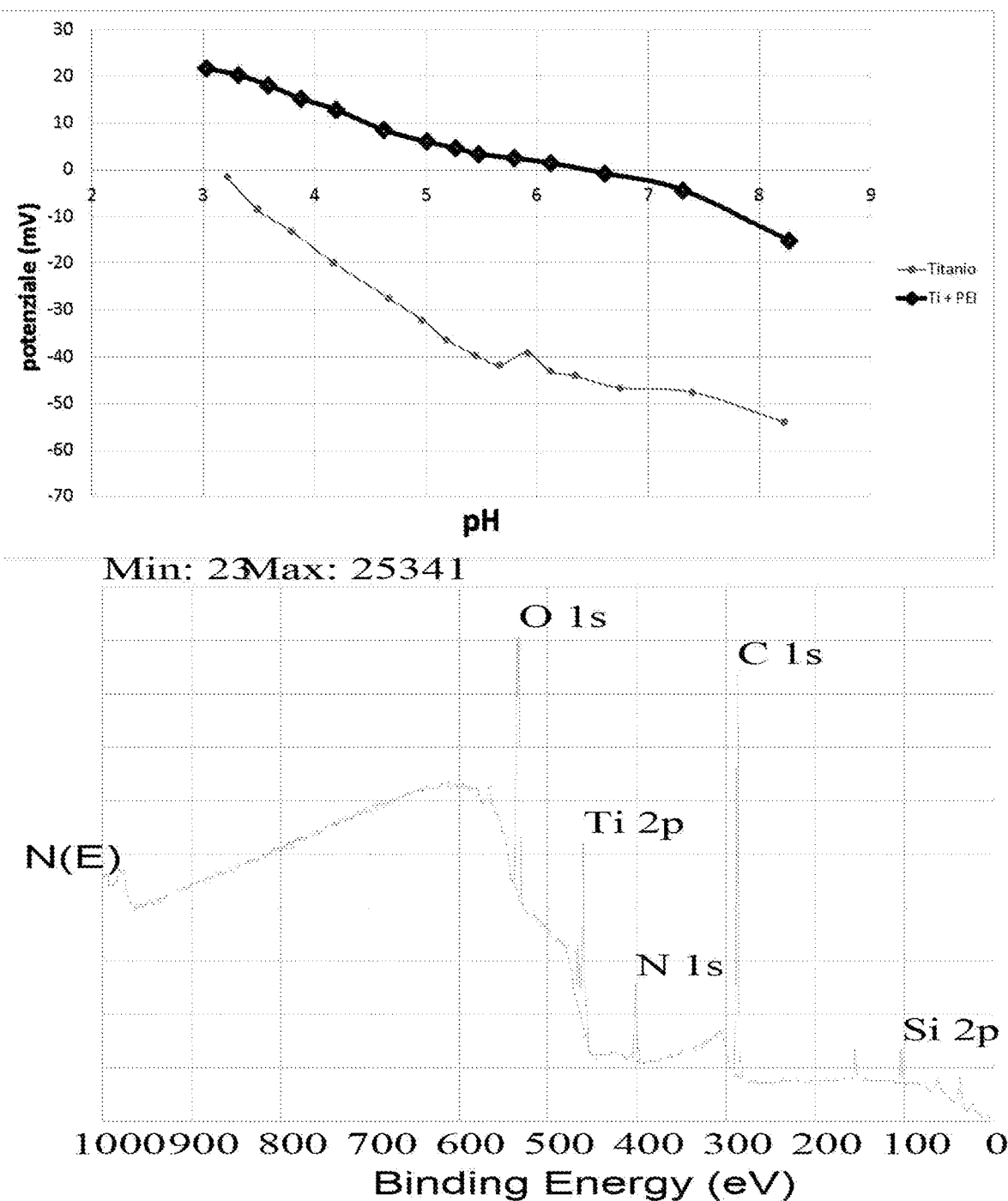
FIG. 2 shows a graph of theta potential as a function of the pH of a Titanium sample functionalized with polyethyleneimine (PEI)

Following the adsorption of PEI, considerable effects are observed on the measured surface chemical parameters, as shown in FIG. 2. The ϑ potential remains negative (and in absolute value much lower than before) only up to the isoelectric point of about pH 6.5.

Afterwards, moving towards the acidic field, the surface takes a positive potential, which is a clear consequence of the presence of the amino groups which, at these pH values, are protonated. The XPS spectrum shows a noticeable N signal, which confirms the successful PEI adsorption, according to the potential data.

The titanium thus functionalized is ready for the subsequent step of coating with biological molecules of plant origin, in particular polyphenols. Titanium samples were evaluated in terms of ϑ potential and of surface chemical composition, functionalized with PEI and then placed in contact with:
- flavonoid with small molecule: epigallocatechin gallate (EGCG);
- polyphenol with large molecule: tannic acid (TA);
- extracts from vinification residues, containing a mixture of polyphenols and other biological molecules of vegetable origin, obtained as described above.

Figure 3:
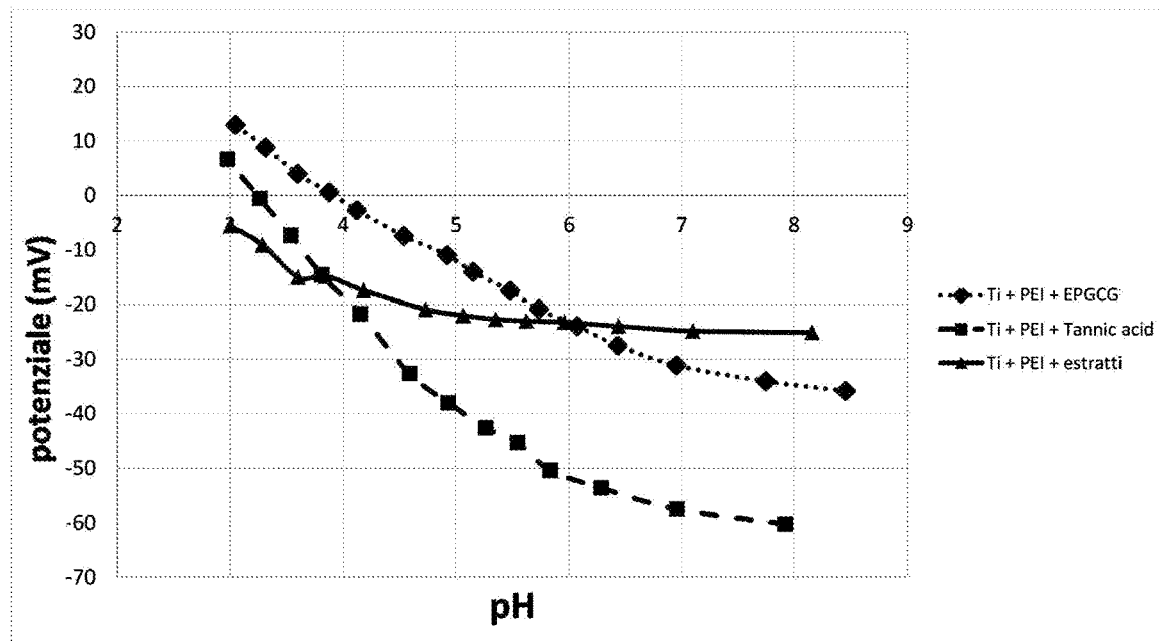
FIG. 3 shows a graph of theta potential as a function of the pH of functionalized titanium samples: Ti+PEI+EPGCG, Ti+PEI+tannic acid and Ti+PEI+extracts from marcs.

To compare the results at the same concentration, all the solutions were made with a polyphenolic content of 2.1 mg/mL GAE. The results shown in FIG. 3 were obtained.

In all three cases there is a return to strongly negative potential at basic pH, as expected due to the introduction on the surface of polyphenolic molecules and from the masking of the PEI groups. However, there are two substantial differences between the samples under examination, namely:

i) the surfaces obtained starting from the pure compounds, Ti+PEI+EGCG and Ti+PEI+TA take positive potential values at acidic pH, suggesting that amine groups are still uncovered and therefore the coating is not complete, unlike the sample obtained starting from extracts. This datum is confirmed by the surface chemical composition value obtained by XPS analysis, which provides the data reported below from the spectra in FIG. 4. As shown in table

TABLE 3

Surface composition (% at) of the samples under examination

| Sample | O | Ti | N | C | Si | coating % |
|---|---|---|---|---|---|---|
| Ti PEI EGCG | 23.2 | 1.4 | 3.4 | 65.2 | 7.1 | 76.7 |
| Ti PEI TA | 29.7 | 1.7 | 2.5 | 60.5 | 5.6 | 71.7 |
| Ti PEI extracts | 26.8 | 0.3 | 1.0 | 65.2 | 6.6 | 95.0 | the Ti signal is virtually absent on the Ti+PEI sample+extract, confirming the most complete coating suggested by the $\vartheta$ potential graphs. The degree of coating (coating %) was calculated using the formula described above, based on a value of Ti % mean=6, obtained as the average of various samples.

The same experiment was repeated with the following samples:
Ti+PEI+morin,
Ti+PEI+quercitrin.

Morin is a water-soluble flavonol (0.25 mg/mL), while quercitrin is insoluble, so it forms a suspension in water. The results of the XPS analysis are as follows:

TABLE 3 bis-Surface composition (% at) of the samples under examination

| Sample | O | Ti | N | C | coating % |
|---|---|---|---|---|---|
| Ti PEI morin | 30.4 | 4.3 | 4.4 | 60.9 | 28.3 |
| Ti PEI quercitrin | 313 | 5.9 | 4.3 | 56.6 | 1.7 | ii) the potential curve of the sample obtained starting from extracts has a plateau, i.e. it reaches an almost constant value from about pH 5.5 upwards. This behavior indicates that on the surface there are homogeneous chemical functions, with acidic behavior, which determine the charge and therefore the surface potential. In fact, the presence of the plateau is caused by the existence of a defined pKa value of the surface functionalities, while the continuous slope trend suggests the existence of multiple pKa or behavior dictated partly by acid-base dissociation of surface functionalities, partly by the adsorption of OH ions.

Basically, these data indicate in a concordant manner that only in the process involving the use of a complex mixture of biological molecules of plant origin, in particular polyphenols, a complete coating with a homogeneously acidic functionality is obtained, characterized by a defined pKa value and not by a range of multiple pKa or phenomena. Considering the nature of the starting molecules, it can be hypothesized that this functionality is phenolic hydroxyl. The process carried out starting from heterogeneous extracts produces surprisingly better results than that carried out starting from pure polyphenolic compounds, either using a flavonoid (EGCG) or a larger and structurally more complex molecule (tannic acid).

Chemical Nature of the Surface Layer

Figure 5:
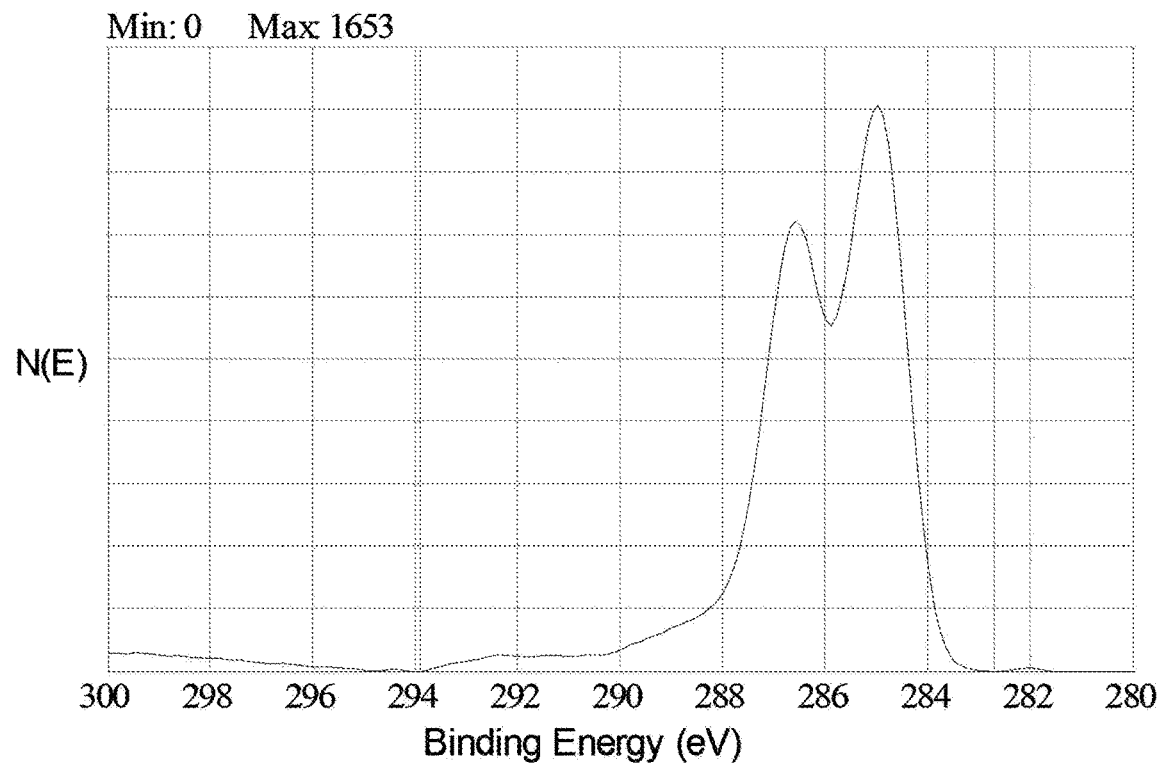
FIG. 5 shows a portion of the XPS spectrum of the sample Ti+PEI+extracts from marcs.
Figure 6:
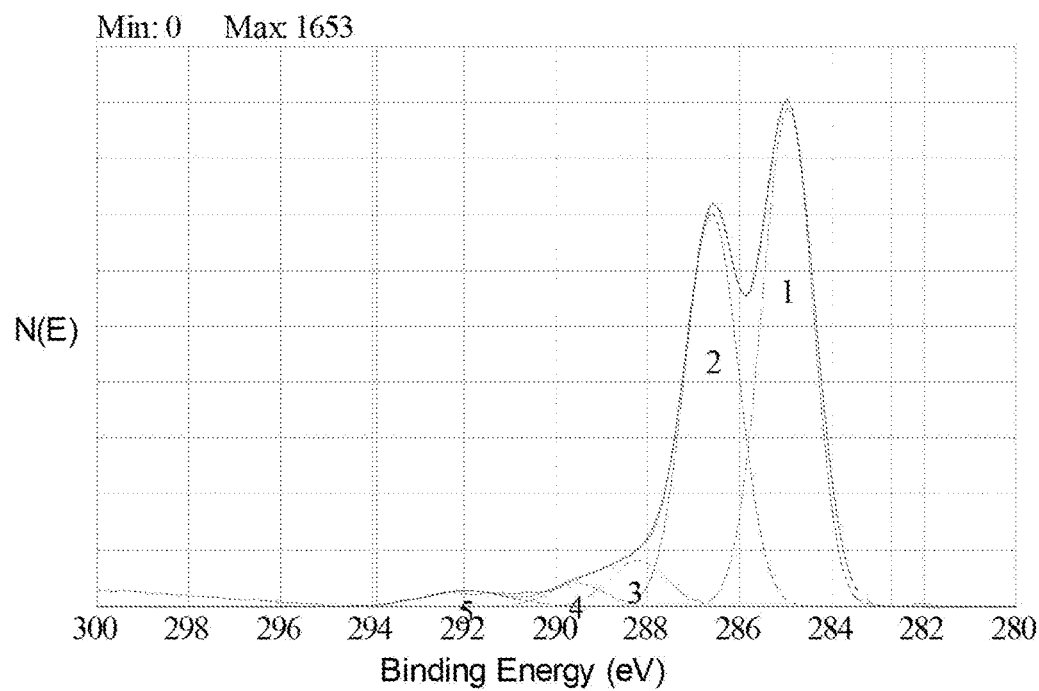
FIG. 6 shows a deconvolution of the spectrum in FIG. 5.

The composition of the starting mixture and the observation, deduced from the $\vartheta$ potential measurements, of a monofunctionally acidic surface, let us suppose that the surface result of the present process is rich in polyphenols. This hypothesis has been corroborated by the XPS measurements, in particular by the detailed study of the shape of the peak C1s, which provides information on the chemical neighborhood of the carbon functionality present. In particular, the peak C1s of the Ti+PEI sample+extract is shown in FIG. 5. The peak is obviously not symmetrical, but consisting of different components. The main one, with a maximum of 285 eV, is notoriously due to carbon atoms linked to other carbon or hydrogen atoms. The single carbon-oxygen bond involves a "shift" of about 1.5 eV and the second component for intensity, with a maximum of about 286.5 eV, is therefore due to C—O functionalities. Each additional oxygen bond involves a shift of about 1.5 eV, whereby carbonyls are at about 288 eV and carboxyls at 289.5 eV. The experimental curve can then be deconvolved as shown in FIG. 6, where components 1, 2, 3 and 4 are due to bonds C—C, C—H, C—O, C=O and OC=O, respectively. From this evaluation it is concluded that the chemical species present on the surface contain a high percentage of CO bonds. The part of the curve between about 291 and 294 eV is difficult to interpret. This datum is very significant, as XPS analyses usually show the so-called shake-up peak in that area, weak and poorly defined (i.e. wide, compared to normal components), due to electronic transitions typical of aromatic rings. The component 5 of the deconvolution curve was then attributed to the presence of aromatic rings.

In essence, the detailed analysis of the peak C1s obtained by the XPS technique of titanium samples surface-functionalized with a process which involves the of adsorption of molecules contained in extracts from vinification residues onto a PEI layer leads to the conclusion that the chemical species present on the surface contain aromatic rings and a considerable number of C—O bonds. It is therefore reasonable to think, even considering that the component in which carboxyls would fall, component 4 in the graph in FIG. 6, is not very abundant in percentage, that the monofunctionally acidic behavior evidenced by the same surfaces by $\vartheta$ potential measurements is due to acidity of the phenolic groups, and that the surface itself mainly consists of polyphenols. Coating density and pKa uniformity are surprisingly better in the case of the present process, performed starting from a heterogeneous mixture of polyphenols and other molecules, compared to what is obtained starting from pure compounds.

Permanence of the Effect Induced by the Adsorption of the Extract Alone Also in Co-Adsorption or Post-Adsorption Processes The following experiment was performed.

The process was carried out as described above, by adsorption on Ti of PEI for two hours and subsequent adsorption overnight from a solution of grape extracts as defined above. Furthermore, samples were prepared in which the following was dissolved in the same solution of extracts:

0.01% (w/v) of hyaluronic acid (HA)
0.05% (w/v) HA
0.3% (w/v) HA.

HA with an average molecular weight of 700-800 kDa was used.

A sample was also prepared which involved the adsorption of a 0.1% solution of HA, without extracts, on Ti+PEI overnight.

Samples were analyzed by XPS analysis and ϑ potential. Table 4 shows the results related to the XPS analysis (Surface composition (% at) of the samples under examination):

| Surface composition (% at) of the samples under examination | | | | | | |
|---|---|---|---|---|---|---|
| Sample | O | Ti | N | C | Si | presence of shake-up component in peak C1s |
| Ti PEI Extracts | 26.8 | 0.3 | 1.0 | 65.2 | 6.6 | yes |
| Ti PEI HA 0.01_Extracts | 28.9 | 0.7 | 1.7 | 67.4 | 1.2 | yes |
| Ti PEI HA 0.05_Extracts | 30.6 | 0.9 | 2.1 | 64.9 | 1.4 | yes |
| Ti PEI HA 0.3_Extracts | 33.7 | 1.3 | 3.3 | 58.5 | 3.2 | yes |
| Ti PEI HA | 34.7 | 3.4 | 6.1 | 50.5 | 5.4 | no |

Figure 7:
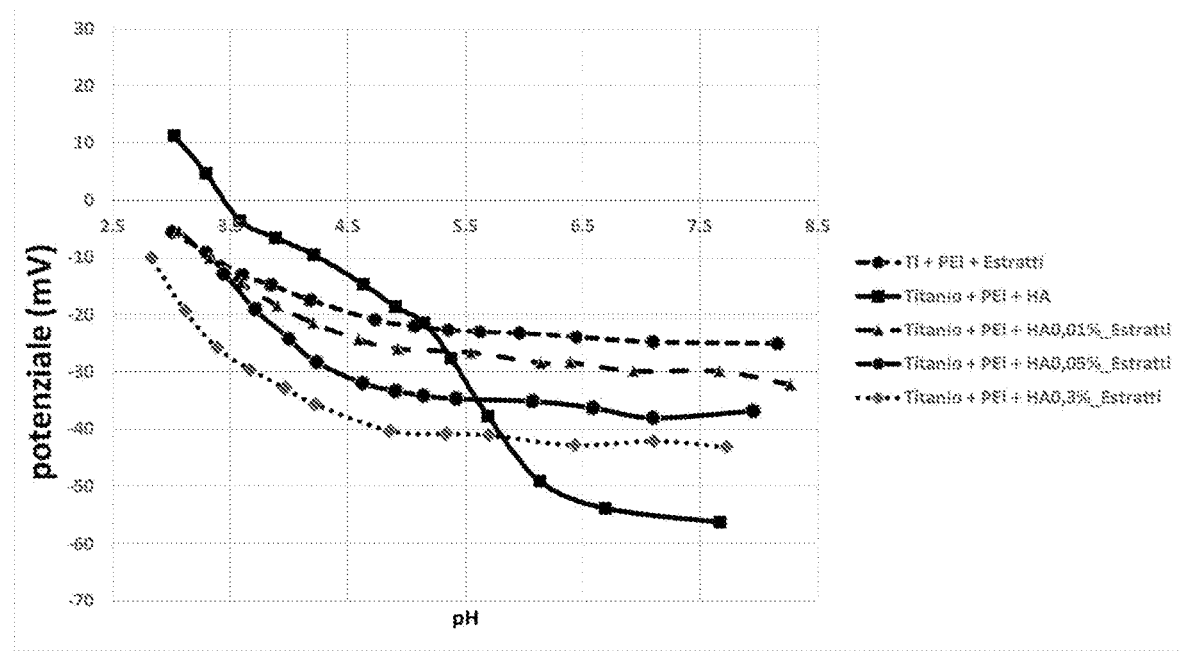
FIG. 7 shows a graph of theta potential as a function of the pH of Ti+PEI samples+extracts of marcs, Ti+PEI+HA and samples obtained by co-adsorption of extracts of marcs and HA at various concentrations.

The data indicate a progressive increase in the C/O ratio, passing from adsorption from pure HA to pure extracts. The surface composition data, together with the analysis of the peak C1s and the evaluation of the presence of the shake-up peak indicate that we are in the presence, for the three intermediate samples, of a phenomenon of co-adsorption, with different surface composition for each of the samples analyzed. The measurement of the ϑ potential provides the results shown in FIG. 7.

In a completely surprising and unpredictable manner, whenever the process starts from the heterogeneous mixture of polyphenols from marcs extracts, even in the presence of co-adsorption of voluminous HA molecules, the measurement denotes the plateau which indicates a monofunctionally acidic surface. This type of surface does not occur in the presence of HA alone, probably because the coating is not as complete and also because the single carboxyl group present in the repeating unit consisting of two monosaccharides is engaged in interacting with the amino groups of PEI and it is not therefore available for an acid-base interface behavior. In the case of polyphenols, the different phenolic groups present on each subcomponent of the molecular unit succeed in producing a homogeneously acidic layer. The absolute value of the plateau potential, linked to the pKa value, increases with increasing concentration of HA in solution, or by direct contribution of the HA molecules to the potential or because the presence of adsorbed HA influences the value of pKa, creating an environment which is more or less favorable to dissociation.

Figure 8:
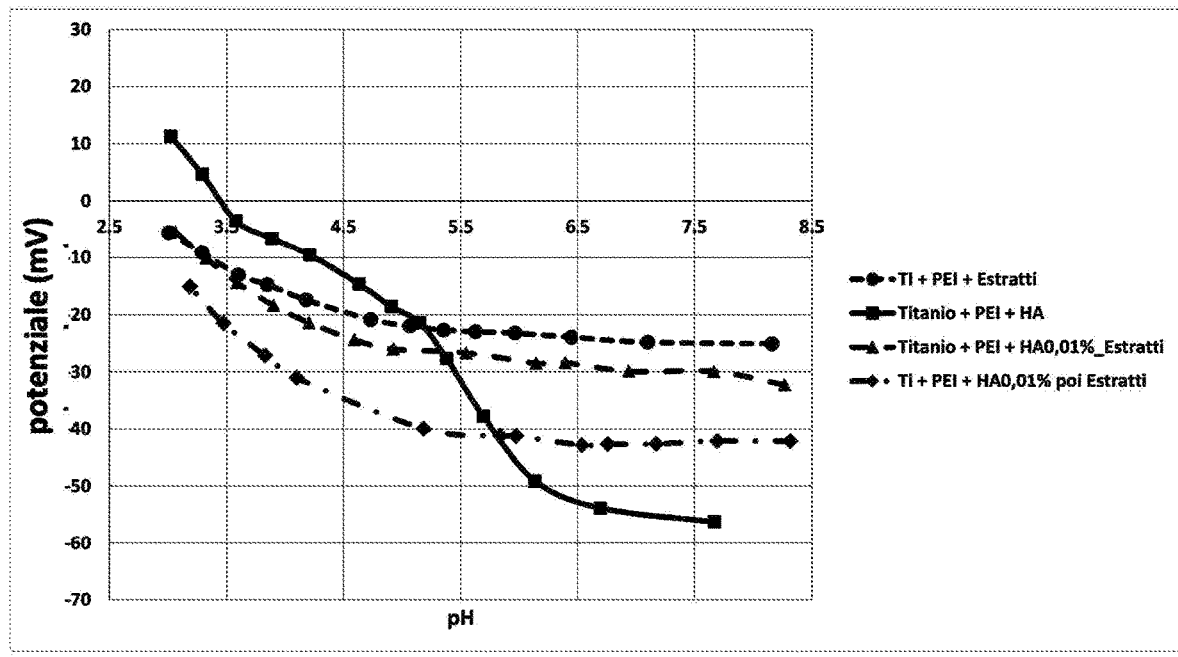
FIG. 8 shows a graph of theta potential as a function of the pH of Ti+PEI samples+extracts of marcs, Ti+PEI+HA and samples obtained by co-adsorption or post-adsorption of extracts of marcs and HA.

The same surprising phenomenon is observed in post-adsorption experiments. In particular, a first layer of PEI is adsorbed on the titanium sample, as in the previous experiments, followed by a layer of HA in 0.01% concentration as in the previous example. At this point, the sample is washed and subjected to further adsorption by marcs extracts overnight. The results are shown in FIG. 8 and in table 5:

| Surface composition (% at) of the samples under examination | | | | | | |
|---|---|---|---|---|---|---|
| Sample | O | Ti | N | C | Si | presence of shake-up component in peak C1s |
| Ti PEI Extracts | 26.8 | 0.3 | 1.0 | 65.2 | 6.6 | yes |
| Ti PEI HA 0.01_Extracts | 28.9 | 0.7 | 1.7 | 67.4 | 1.2 | yes |
| Ti PEI HA 0.01 then extracts | 32.8 | 1.1 | 4.6 | 57.9 | 3.6 | yes |
| Ti PEI HA | 34.7 | 3.4 | 6.1 | 50.5 | 5.4 | no |

The data indicate that also on a surface already coated with hyaluronic acid molecules, the polyphenols present in the heterogeneous mixture of extracts are adsorbed on the surface and organize a structure which imparts a monofunctionally acidic behavior to the surface itself. Surface composition and ϑ potential value are different in the case of co- and post-adsorption but, surprisingly, in both cases the surface has a defined pKa value. This observation supports the hypothesis that, regardless of the nature of the adsorbent surface (pure PEI or PEI which has already adsorbed HA and therefore has partially saturated surface sites) the supply, in terms of molecular species, provided by the heterogeneous mixture of polyphenols is such as to always allow the selection by the surface of the species with greater affinity for it, optimizing space encumbrance and interaction energy so as to always arrive, starting from the most disparate conditions (presence of other molecules in solution or surface), to create a functionally homogeneous surface layer. This result cannot be anticipated from what is reported in the prior art.

Figure 9:
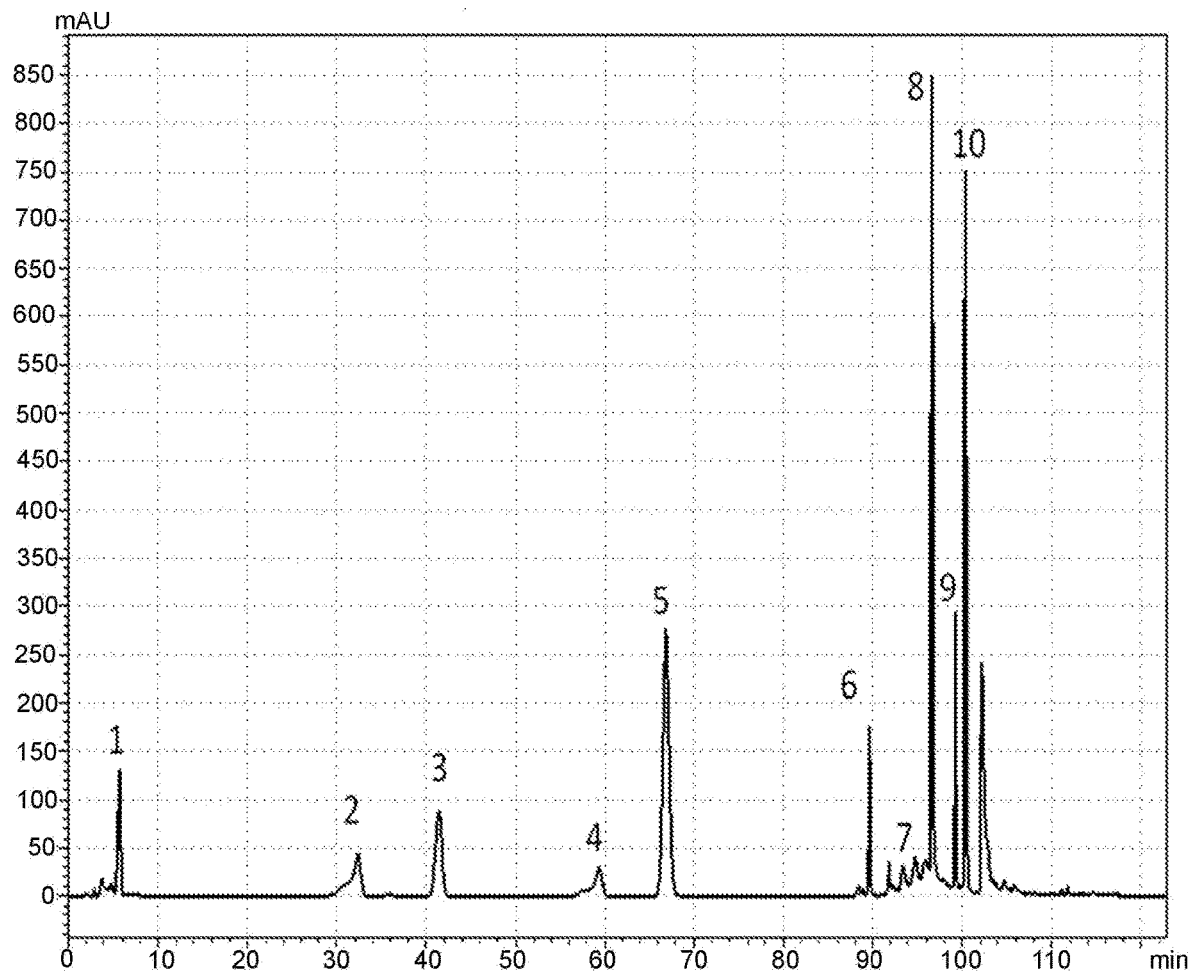
FIG. 9 shows the chromatogram of a recreated polyphenol mixture.

A further test is carried out as a proof of this in which the same process is used, with adsorption from a solution containing a MIX of pure polyphenolic compounds. In particular, molecules of different molecular weight and structure are used to simulate the adsorption from the heterogeneous mix of the marcs extract. The composition of the MIX, for a value of 2.05 mg/mL GAE, and the relative chromatogram are shown in FIG. 9 and in table 6:

| | |
|---|---|
| 1. Gallic acid | 150 ug/cc |
| 2. Caffeic acid | 200 ug/cc |
| 3. Coumaric acid | 200 ug/cc |
| 4. Catechin | 200 ug/cc |
| 5. EPGCG | 150 ug/cc |
| 6. Rutin | 200 ug/cc |
| 7. Tannic acid | 250 ug/cc |
| 8. Trans-Resveratrol | 150 ug/cc |
| 9. Quercetin | 200 ug/cc |
| 10. Trans-Cinnamic acid | 250 ug/cc |

Figure 10:
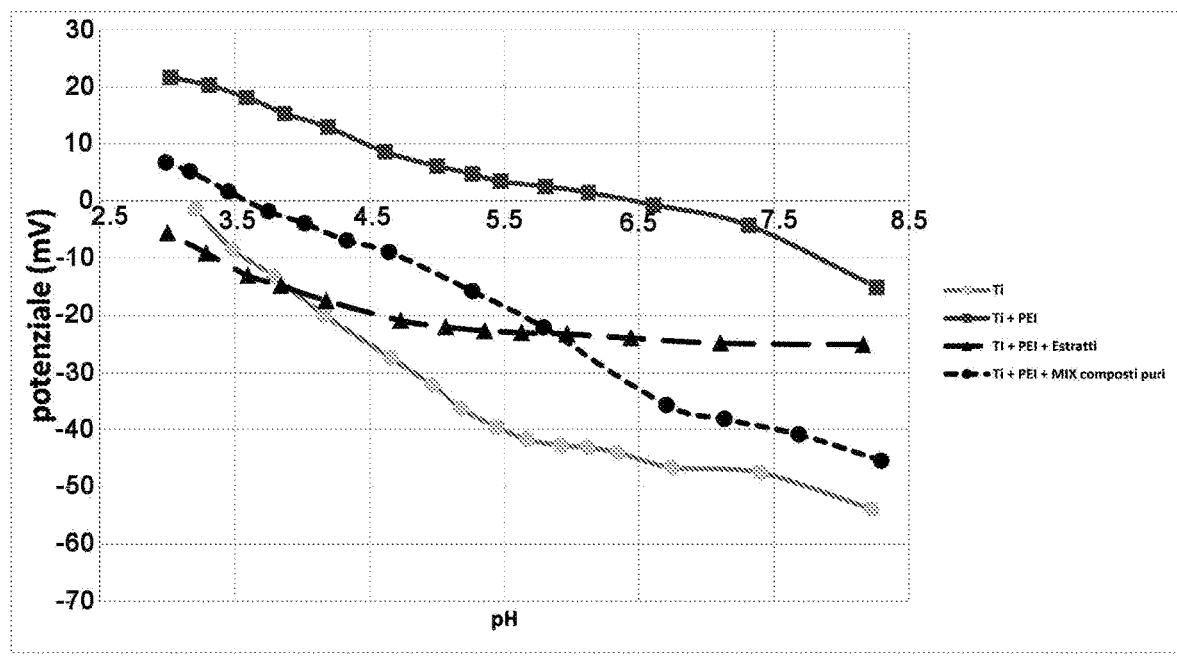
FIG. 10 shows a graph of theta potential as a function of the pH of Ti+PEI samples+extracts of marcs and Ti+PEI+mixture of polyphenols in FIG. 9.

The measurement of the ϑ potential provides the results shown in FIG. 10.

The successful adsorption of the MIX compounds is confirmed by the almost totally negative field transition (apart for pH<3.5) of the ϑ potential value of the Ti+PEI sample+MIX of pure compounds, which on Ti+PEI is instead mostly positive, as expected. On Ti+PEI+MIX, however, no plateau is observed: the phenolic groups adsorbed to the surface have a Ka range and the surface structure is substantially different from that obtained by the process of the invention.

Figure 11:
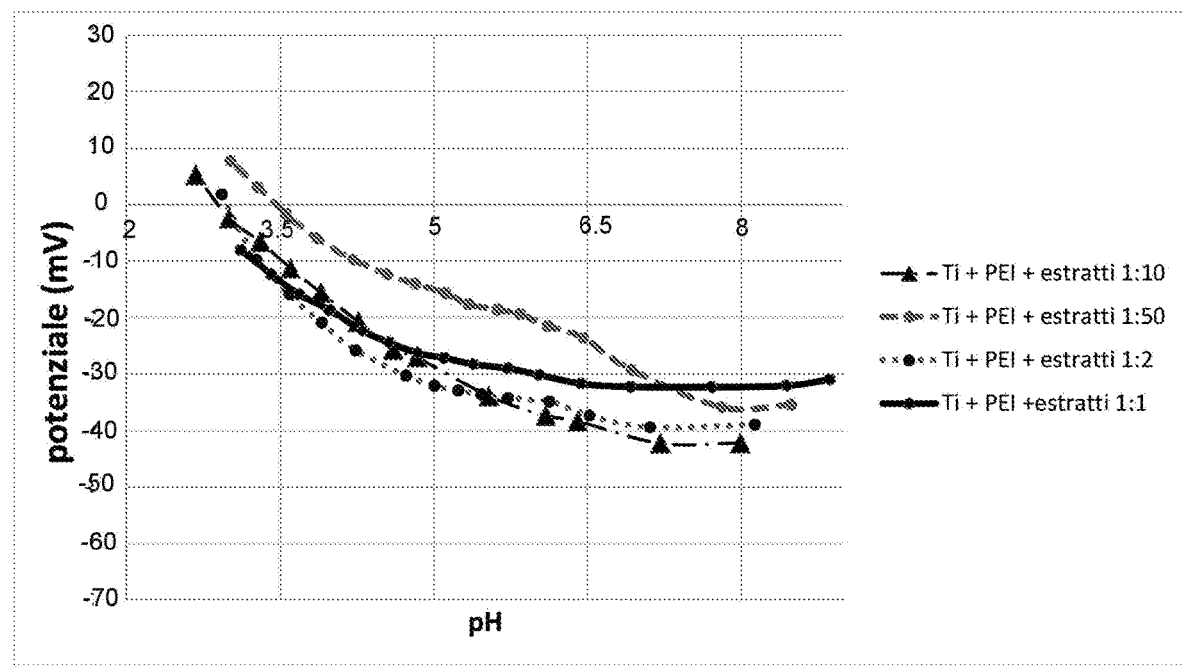
FIG. 11 shows a graph of theta potential as a function of the pH of Ti+PEI samples+extracts of marcs at various extract concentrations.

While in the case of pure compounds, the formation of plateau is not observed, in the case of adsorption from extracts the permanence of notable effects is surprisingly observed on the value and shape of the ϑ potential curve also with considerable dilutions of the adsorption solution. The graph in FIG. 11 reveals that by diluting the solution of extracts 1:2, 1:10 and 1:50 there are significant deviations from the plateau trend only in the case of the strongest dilution, which however preserves considerable evidence of superficial negative charge.

taken and placed in microwells (48 multiwells). The absorbance of the solution is read with a Tecan Spark 10M microplate reader (Tecan), in the spectral range from 276 to 380 nm. For the evaluations, the wavelengths of 280 nm are used, in which they absorb most of the polyphenols, 370 nm, where quercetin, widely present in the extracts, has a maximum and 355 nm, where there is the maximum peak of rutin. The following results are obtained, reporting the absorbance values measured in the release solution of each of the three replicates used for each sample type in table 8:

| | Sample | | | | | | | | | | | |
|---|---|---|---|---|---|---|---|---|---|---|---|---|
| | Ti PEI Extracts | | | Ti PEI Extracts 0.1% HA | | | Ti PEI | | | Ti | | |
| λ (nm) | n. 1 | n. 2 | n. 3 | n. 1 | n. 2 | n. 3 | n. 1 | n. 2 | n. 3 | n. 1 | n. 2 | n. 3 |
| 280 | 3.212 | 3.229 | 3.152 | 3.194 | 3.210 | 3.240 | 3.239 | 3.207 | 3.213 | 3.185 | 3.170 | 3.206 |
| 355 | 0.217 | 0.210 | 0.213 | 0.215 | 0.208 | 0.208 | 0.214 | 0.210 | 0.211 | 0.211 | 0.209 | 0.212 |
| 370 | 0.110 | 0.106 | 0.106 | 0.107 | 0.104 | 0.104 | 0.107 | 0.106 | 0.104 | 0.106 | 0.104 | 0.106 |

Basically, taking into account the high dilutions used, the data confirm a surprising affinity of the extracts for the titanium surface functionalized with PEI, decidedly and surprisingly higher than that found in the case of pure compounds. This is confirmed by the XPS analysis data obtained on the same samples, which show a considerable coating of the titanium of the surface even in the case of high dilutions, as shown in table 7:

| Surface composition (% at) of the samples under examination | | | | | |
|---|---|---|---|---|---|
| Sample | O | Ti | N | C | Si |
| Ti PEI extracts | 26.8 | 0.3 | 1.0 | 65.2 | 6.6 |
| Ti PEI extracts 1:2 | 26.7 | 0.6 | 1.6 | 63.6 | 7.7 |
| Ti PEI extracts 1:10 | 27.9 | 0.9 | 2.7 | 58.6 | 9.9 |
| Ti PEI extracts 1:50 | 27.7 | 3.9 | 1.4 | 59.9 | 7.1 |

Absence of Release of Adsorbed Molecules

For the reasons described above, the polyphenols immobilized to the titanium surface according to the present process have a remarkable stability and are not desorbed in aqueous solution even in the absence of covalent bonds as described in the prior art. This feature is demonstrated by carrying out the experiment reported in WO 2014169959 A1, i.e. immobilizing polyphenolic molecules on titanium discs, placing the discs in PBS (Phosphate Buffered Saline) and reading the absorbance at a given wavelength by UV-vis absorption spectroscopy. In particular, using titanium discs of 6 mm diameter, three replicates are prepared as follows:
  i- titanium as such,
  ii- titanium on which PEI is adsorbed from a 0.5% aqueous solution for 2 hours,
  iii- as sample ii, with further adsorption overnight from a solution of marcs extracts,
  iv- as a sample ii, with further adsorption overnight from a solution of marcs extracts containing 0.1% (wt/vol) of hyaluronic acid with an average molecular weight of 700-800 kDa.

After drying, the discs are placed individually in the wells of a polystyrene plate with 48 microwells for cell cultures, immersed in 500 μL of PBS. After 72 h, 400 μL of PBS are The analysis of variance, performed in a one-way manner comparing the measured data at each wavelength, indicates that in no case the average values measured on the four samples under examination are significantly different. In essence, the presence in PBS of polyphenol-coated discs according to the present process does not entail significant alterations in the absorbance measured at the absorption wavelengths typical of polyphenols. This data therefore indicates that polyphenols are not released from the coated discs.

Creation of Multiple Layers

A second significant technological advantage of the present process is the possibility of producing polycationic-polyanionic multilayers. As known and described in the prior art (e.g. Picart, C.; Lavalle, P.; Hubert, P.; Cuisinier, F. J. G.; Decher, D.; Schaaf, P.; Voegel, J.-C. *Buildup mechanism for poly(L-lysine)/hyaluronic acid films onto a solid surface*, Langmuir 2001, 17, 7414-7421), the surface features of a material can be modified by a sequential adsorption process of a polycation, typically PEI, followed by that of a polyanion (hyaluronic acid, heparin, polysaccharides, polyacrylic acid or others). At this point, it is possible to repeat the sequence, with a new PEI adsorption to the polyanionic surface, followed by a new polyanion adsorption, up to a defined number of layers. The main advantage of this sequential process is that an even more complete and uniform coating of the surface is thus obtained.

We have verified that, surprisingly, the construction of a polycation-polyanion multi-layer is effectively possible only by starting from the marcs extracts of the invention, not from pure polyphenols, as can be derived from the experiment described herein.

Figure 12:
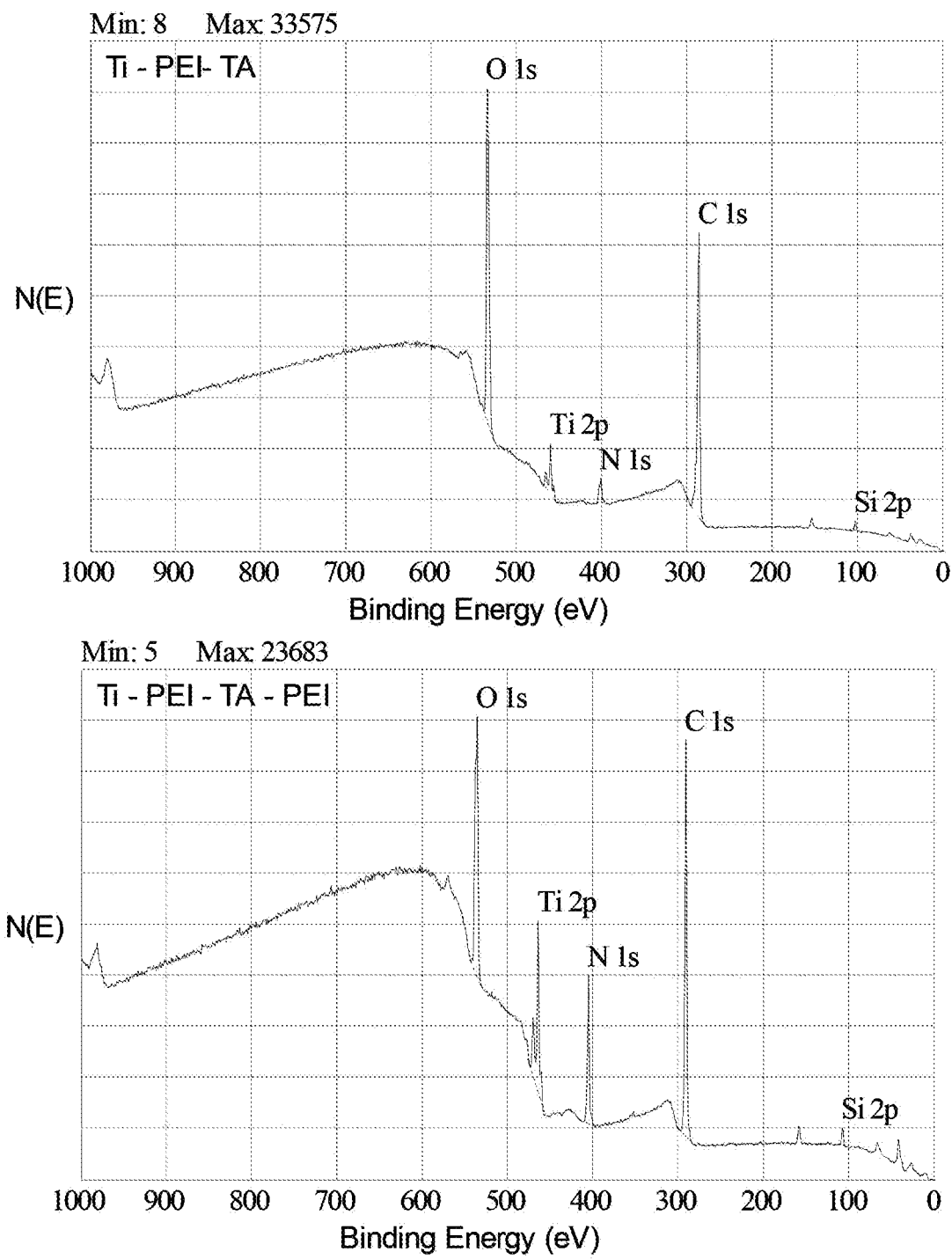
FIG. 12 shows the XPS spectra of a Ti+PEI+TA sample and of a Ti+PEI+TA+PEI sample (TA=tannic acid)

Using the methods described above, a Ti+PEI+TA (tannic acid) sample is produced, thus using a large polyphenolic molecule which should impart greater stability to the construct and provide a more complete coating than small molecules. The XPS analysis shows a spectrum similar to that in FIG. 4, confirming the successful adsorption of TA to the surface. At this point, a further layer of PEI is applied, by adsorption for 2 hours from a 0.5% aqueous solution, the sample is dried and the XPS analysis is performed, obtaining the result shown in FIG. 12.

The spectrum of Ti+PEI+TA+PEI shows a remarkable titanium signal and a strong nitrogen signal. Comparing it with that of Ti+PEI+TA, the only explanation is that the molecules of PEI in solution have replaced those of TA on the surface, so that the PEI-TA interaction is not so strong as to constitute a stable substrate for the further PEI layer.

Figure 13:
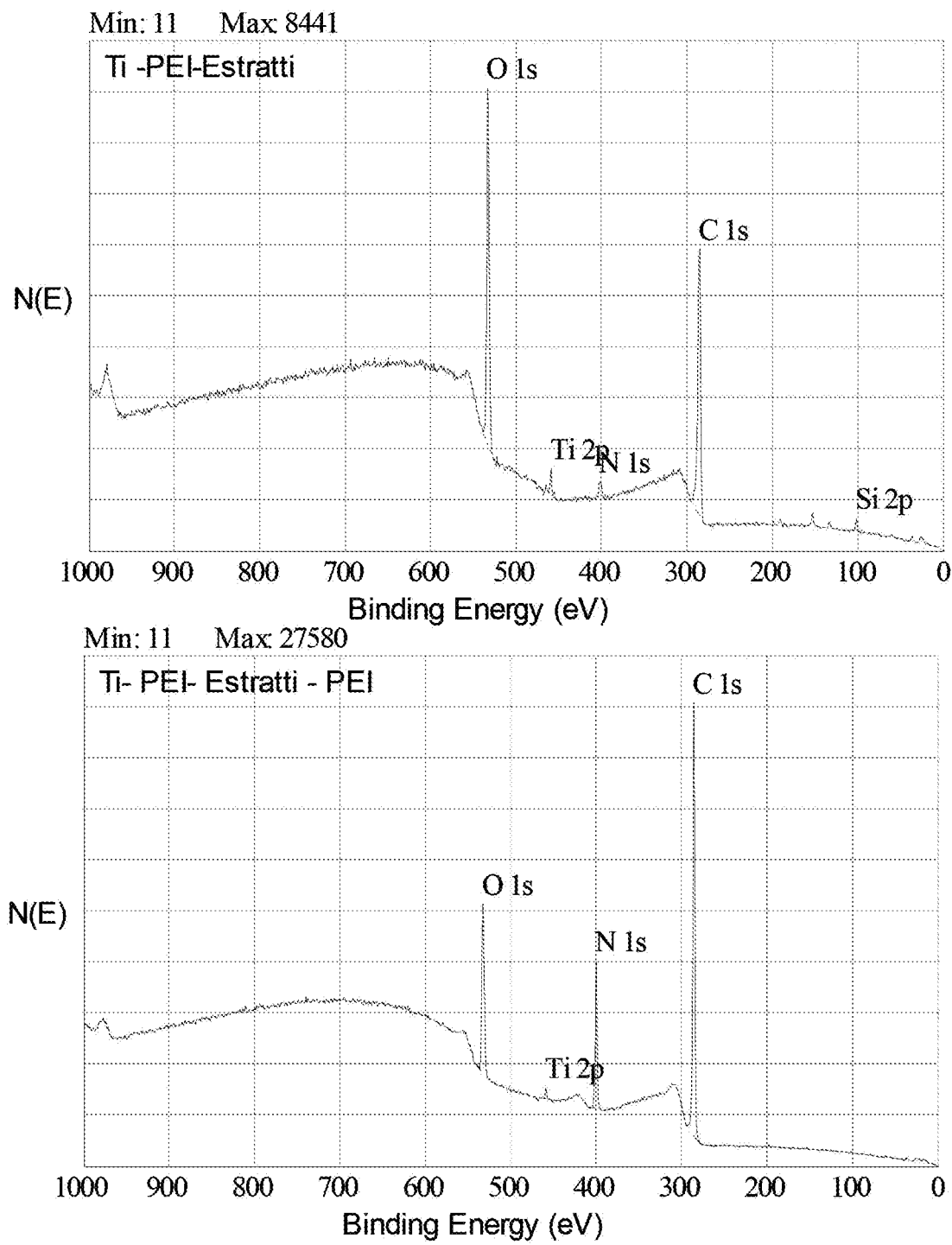
FIG. 13 shows the XPS spectra of a Ti+PEI sample+extracts of marcs and of a Ti+PEI sample+extracts of marcs+PEI.
Figure 14:
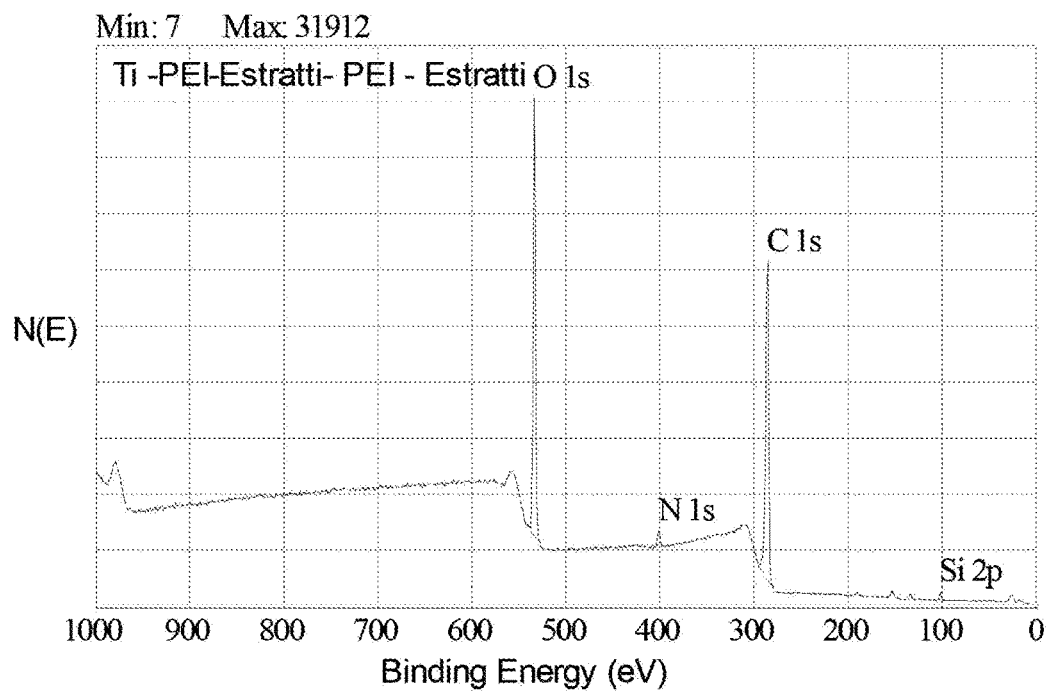
FIG. 14 shows the XPS spectrum of a Ti+PEI sample+extracts of marcs+PEI+extracts of marcs.

Repeating the same experiment on the sample made with marcs extracts gives the results shown in FIG. 13. The evidence is completely different from the previous case. We observe the expected increase in the C/O ratio, the expected increase in the N signal and only a very low Ti signal is present. These data indicate that a further layer of PEI has adsorbed on the anionic surface obtained from the extracts and that the set is stable, unlike that obtained with a single molecule, although large as TA of the previous case. At this point a further anionic layer can be applied, repeating adsorption from marcs extracts. The result shown in FIG. 14 is obtained.

Figure 15:
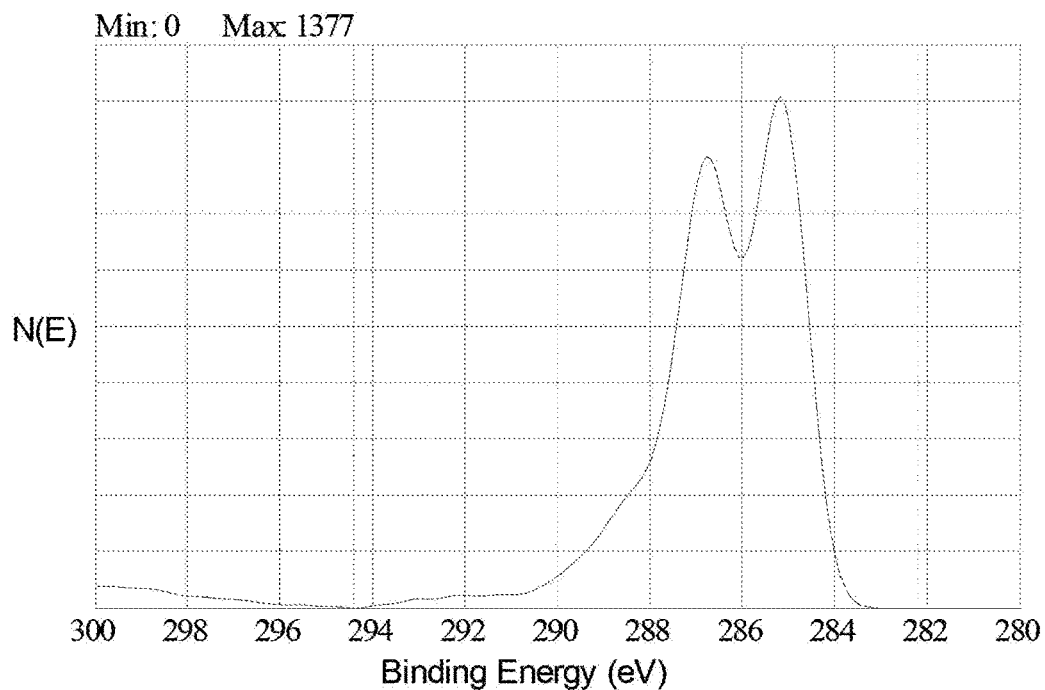
FIG. 15 shows an amplified portion of the XPS spectrum of the sample in FIG. 14.

The increase in the O/C ratio, the decrease in absolute value of the PEI signal and the disappearance of the Ti signal are again observed. We then return to a typical composition of the adsorbed extracts, as also confirmed by the peak C1s which shows a significant CO component and the shakeup peak, as discussed above (FIG. 15).

The stability features of the first anionic layer, taken from the previous structural data and the absence of release, allow in this case the construction of successive polycationic-polyanionic layers. As discussed above, they allow an even more complete and homogeneous coating, as evidenced by the disappearance of the Ti signal and the shape of the general spectrum, which at high b.e. appears flat and not curved, as in the previous cases, due to the minor electronic density of the molecular layer compared to the metal one. The measurements of $\vartheta$ potential also provide the plateau trend, even in this case. The surface in FIG. 14 is homogeneously polyphenolic and monofunctionally acidic, to a greater extent than described in the prior art and in a not anticipated manner.

Biological Effects

Cell culture growth tests were conducted to evaluate the biological effects of the surface structure achieved with the present process. In particular, the process was adopted to functionalize the surface of polystyrene microplates for cell cultures. L929 fibroblast cell growth experiments were performed according to the following protocol.

The cells used are fibroblasts of mouse connective tissue L-929 (BS CL 56), purchased at the Cell Substrate Center of the Istituto Zooprofilattico Sperimentale of Lombardy and Emilia Romagna.

A suspension of fibroblasts (whose density was calculated using the TC10 Automated Cell Counter instrument, BIO-RAD) in 3.0 mL of Minimum Essential Medium+glutaMAX medium (MEM-glutaMAX), supplemented with 10% bovine fetal serum (FBS), penicillin and streptomycin (all components of the GIBCO cell growth medium come from the company LIFE TECHNOLOGIES Srl, San Giuliano Milanese (MI)), was introduced in sterile polystyrene containers for cell cultures with 24 compartments (24 multiwell plate, Sarstedt). Each of the wells had been subjected to the surface modification process, as described below. All the operations described were conducted under laminar flow hood (Faster BIO 48, DASIT).

The 12-well containers were then placed in a HERA CELL incubator (HERAEUS) at 37° C., 5% $CO_2$ and relative humidity of 98% for the defined times.

At the expected experimental time, the cells were observed under the inverted optical microscope DMI4000 B (LEICA) to obtain qualitative indications on the course of the test. They were then subjected to quantitative assessment of viability by MTT tests, for the evaluation of the efficiency of the mitochondrial succinate dehydrogenase enzyme (SDH). The MTT test provides that, after microscopic observation, the cells are incubated with a solution of 5 mg/ml of the soluble tetrazolium salt 3-(4.5-dimetiltiazol-2-yl)-2,5-diphenyl tetrazolium bromide, Sigma Aldrich Srl, Milan. The succinate dehydrogenase enzyme, during the three subsequent incubation hours at 37° C., induces the transformation of the tetrazolium salts, initially in soluble and yellow form, into a blue water-insoluble product, formazan: the greater is the amount of precipitate, the higher the enzymatic activity, and therefore the number of metabolically viable cells. The precipitate is solubilized with dimethyl sulfoxide (Sigma Aldrich Srl, Milan) and measured spectrophotometrically at 560 nm wavelength using a SPARK 10M spectrophotometer (TECAN ITALIA srl).

Results

In a first experiment, the following samples were prepared:

polystyrene microwell functionalized with a single layer of polyphenols adsorbed on PEI (4 replicates, referred to as Extracts 1);

polystyrene microwell functionalized with a single layer of tannic acid adsorbed on PEI (4 replicates, referred to as TA).

The non-functionalized microwell was used as a control, i.e. a specific surface for cell cultures (4 replicates, referred to as TCPS)

The initial inoculum was $3 \times 10^5$ cells/mL.

Cell growth was evaluated at 48 h, obtaining the results shown in table 9, followed by one-way variance analysis and post hoc Tukey HSD test for the verification of significance.

TABLE 9

| Sample | Ads. 1 | Ads. 2 | Ads. 3 | Ads. 4 | Mean | Std |
|---|---|---|---|---|---|---|
| TCPS | 0.985 | 0.857 | 1.105 | 1.120 | 1.017 | 0.122 |
| Extracts 1 | 1.271 | 1.098 | 1.210 | 1.460 | 1.260 | 0.151 |
| TA | 0.941 | 0.965 | 0.874 | 1.015 | 0.949 | 0.059 |

Anova: F = 7.75;
p = 0.0011037
HSD[.05] = 0.23;
HSD[.01] = 0.32
M1 vs M2 P < .05
M1 vs M3 nonsignificant
M2 vs M3 P < .05

The result indicates that the surface structure implemented according to the present process allows a better cell growth with respect to the TCPS control and to the structure obtained using the pure polyphenolic molecule (tannic acid).

In a second experiment, the following samples were prepared according to the method described above:

polystyrene microwell functionalized with a single layer of polyphenols adsorbed on PEI (4 replicates, referred to as Extracts 1);

polystyrene microwell functionalized with a double layer of polyphenols adsorbed on PEI (4 replicates) (PEI-extracts-PEI-extracts, referred to as Extracts 2).

The non-functionalized microwell was used as a control, i.e. a specific surface for cell cultures (4 replicates, referred to as TCPS).

The initial inoculum was $2 \times 10^4$ cells/mL.

Cell growth was evaluated at 48 h, obtaining the results shown in table 10, followed by one-way variance analysis and post hoc Tukey HSD test for the verification of significance.

TABLE 10

| Sample | Ads. 1 | Ads. 2 | Ads. 3 | Ads. 4 | Mean | Std |
|---|---|---|---|---|---|---|
| TCPS | 0.413 | 0.527 | 0.471 | 0.418 | 0.457 | 0.053 |
| Extracts 1 | 0.640 | 0.517 | 0.619 | 0.687 | 0.616 | 0.072 |
| Extracts 2 | 0.698 | 0.748 | 0.761 | 0.746 | 0.738 | 0.028 |

Anova: F = 27.2;
p = 0.000153
HSD[.05] = 0.11;
HSD[.01] = 0.15
M1 vs M2 P < .01
M1 vs M3 P < .01
M2 vs M3 P < .05

The experiment proves the stimulation of cell growth by both Extracts 1 and Extracts 2 samples, but shows that the Extracts 2 sample, i.e. the multilayer, provides the greatest stimulation of cell growth.

Modulation of Surface Properties by Co-Adsorption

An experiment is conducted as shown above, to verify the effect of a co-adsorption of marcs extract and hyaluronic acid on titanium substrate on cell proliferation. The initial inoculum was $8 \times 10^4$ cells/mL. The results of the experiment, after 48 hours of incubation, are shown in table 11:

| Sample | Ads. 1 | Ads. 2 | Ads. 3 | Mean | Std |
|---|---|---|---|---|---|
| TCPS | 0.760 | 0.786 | 0.850 | 0.799 | 0.046 |
| Extracts 1 | 0.920 | 1.004 | 0.981 | 0.968 | 0.043 |
| Extracts 1 + 0.01% HA | 0.957 | 0.982 | 0.973 | 0.971 | 0.012 |
| Extracts 1 + 0.05% HA | 0.752 | 0.829 | 0.795 | 0.792 | 0.039 |

Anova: F = 21.38; p = 0.000355
HSD[.05] = 0.1; HSD[.01] = 0.13
M1 vs M2 P < .01
M1 vs M3 P < .01
M1 vs M4 nonsignificant
M2 vs M3 nonsignificant
M2 vs M4 P < .01
M3 vs M4 P < .01

The datum indicates that cell adhesion and growth are modulated by the features of the layer used, while always remaining in the presence of a monofunctionally acidic polyphenolic layer. According to the anti-adhesive properties of HA, its progressive introduction leads to a decrease in the measured values. The layer obtained with extracts alone is not significantly different than that obtained by adding 0.01% HA, both are significantly different than that obtained by adding 0.05% HA, which has lower adhesion and proliferation. It is also important to underline the notable effect of the composition of the surface layer on the cellular morphology. The cells present on Extracts 1+0.05% HA do not take the flattened and enlarged morphology of well-adherent cells, but retain a globular appearance, similar to that taken on HA layers.

Experimental Tests on Extracts of Different Grapes

The extraction process, as described above, was repeated using marcs from four different grapes. In addition to the aforementioned Nebbiolo from Barbaresco, involved in the first part of the experimentation, the following were evaluated:

Marcs from Barbera, area of production Portacomaro (AT);
Marcs from Croatina, red grapes very rich in anthocyanins, area of production Cisterna (AT);
Marcs from Arneis, white grapes, area of production Cisterna (AT).

The extracts, obtained by the method indicated above, were characterized as shown in table 12:

| Grape | DPPH [%] | FC [mg/ml GAE] | Total anthocyanins [mg/l] | Gallic acid [mg/l] | Quercetin [mg/l] | Rutin [mg/l] | Malvidin-3-glucoside [mg/l] |
|---|---|---|---|---|---|---|---|
| Nebbiolo | 44.33 | 3.44 | 74.4 | 19.43 | 66.46 | 38.45 | 3.76 |
| Barbera | 64.21 | 2.30 | 89.25 | 20.42 | 16.62 | 16.71 | 21.15 |
| Croatina | 83.52 | 2.12 | 449.75 | 12.70 | 20.42 | 38.01 | 435.12 |
| Arneis | 36.21 | 2.42 | 14.87 | 2.31 | 2.62 | 26.60 | 0.00 |

The data confirm the abundance of anthocyanins in Croatina and their low presence in the white marcs of Arneis.

General Information about the Process

Using the extracts of the different grapes mentioned above, the polyphenols adsorption experiments on titanium were repeated. As described in the first part, the process involves the functionalization of titanium by adsorption of polyethyleneimine (PEI) from aqueous solution at room temperature for 2 h. After the functionalization has been carried out, the washing is carried out and the material is put into contact with the aqueous solution of the extracts overnight at room temperature; the extracts are diluted if necessary so as to obtain a starting value of CF close to 2. The material is then washed and characterized by XPS analysis and measurement of the 9 potential. The XPS analysis data are shown in table 13:

| Surface composition (% at) of the samples under examination | | | | | |
|---|---|---|---|---|---|
| Sample | O | Ti | N | C | Si |
| Ti PEI Nebbiolo | 26.8 | 0.3 | 1.0 | 65.2 | 6.6 |
| Ti PEI Croatina | 27.5 | 0.4 | 2.0 | 67.8 | 2.3 |
| Ti PEI Barbera | 29.5 | 0.8 | 2.3 | 63.7 | 3.8 |
| Ti PEI Arneis | 22.8 | 0.5 | 1.1 | 74.0 | 1.6 |

Figure 16:
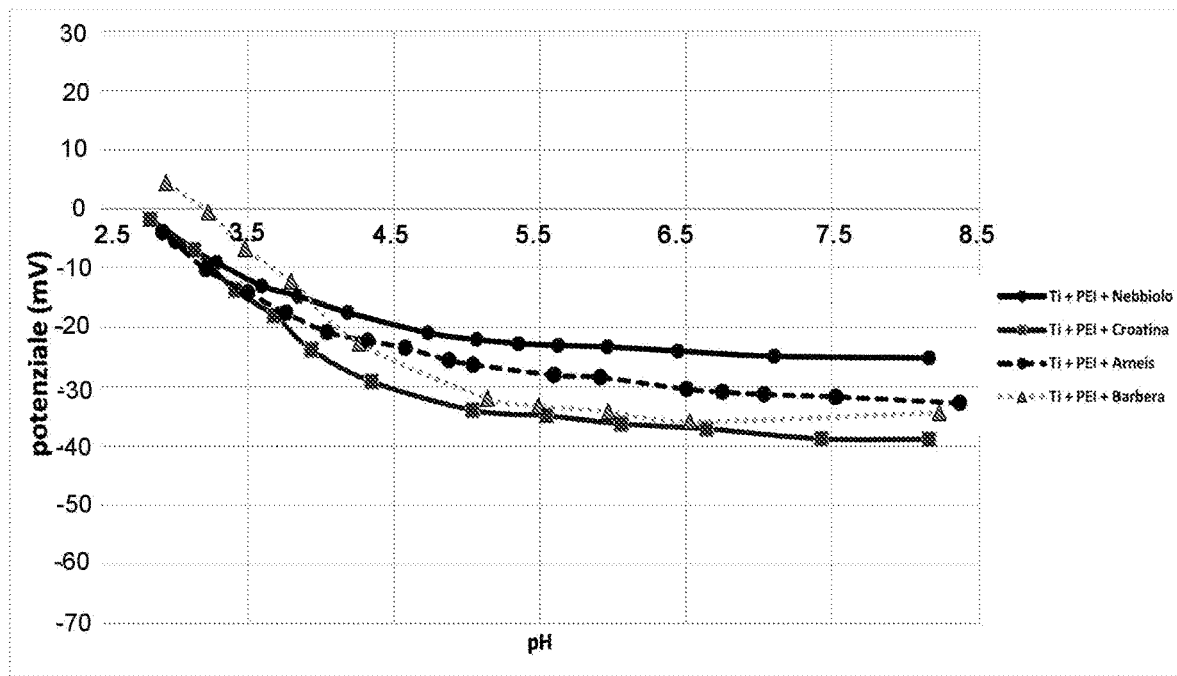
FIG. 16 shows a graph of theta potential as a function of the pH of Ti+PEI samples+extracts of marcs of nebbiolo, barbera, croatina and arneis.
Figure 17:
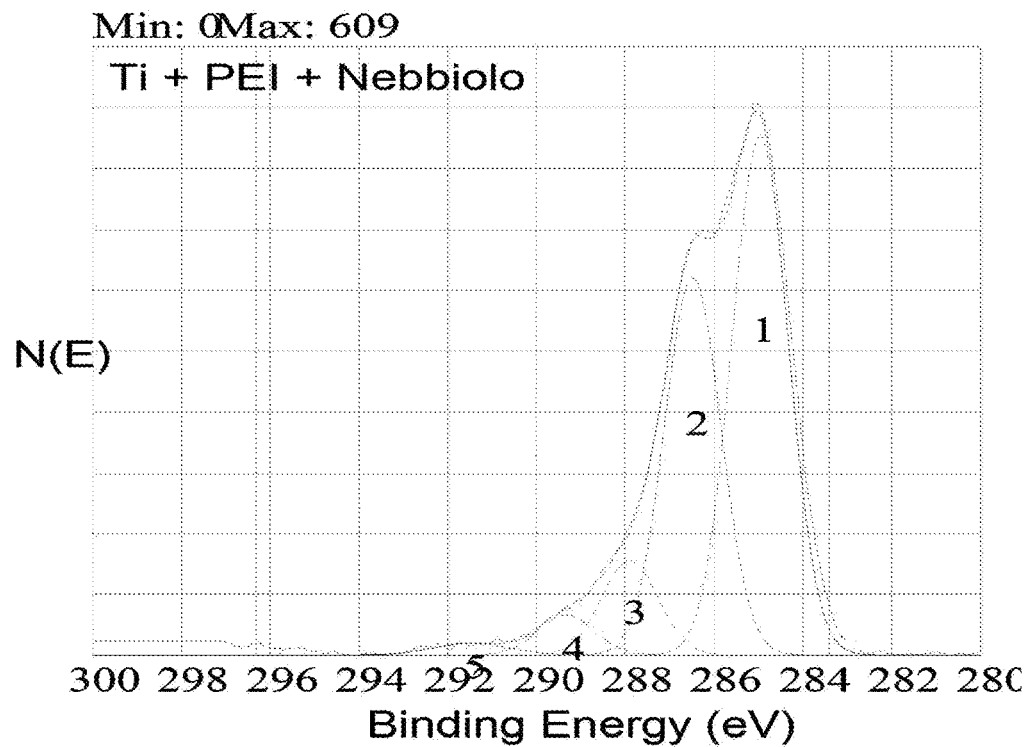
FIGS. 17-20 show the deconvolution of a portion of the XPS spectrum of the samples in FIG. 16 in the indicated order.
Figure 18:
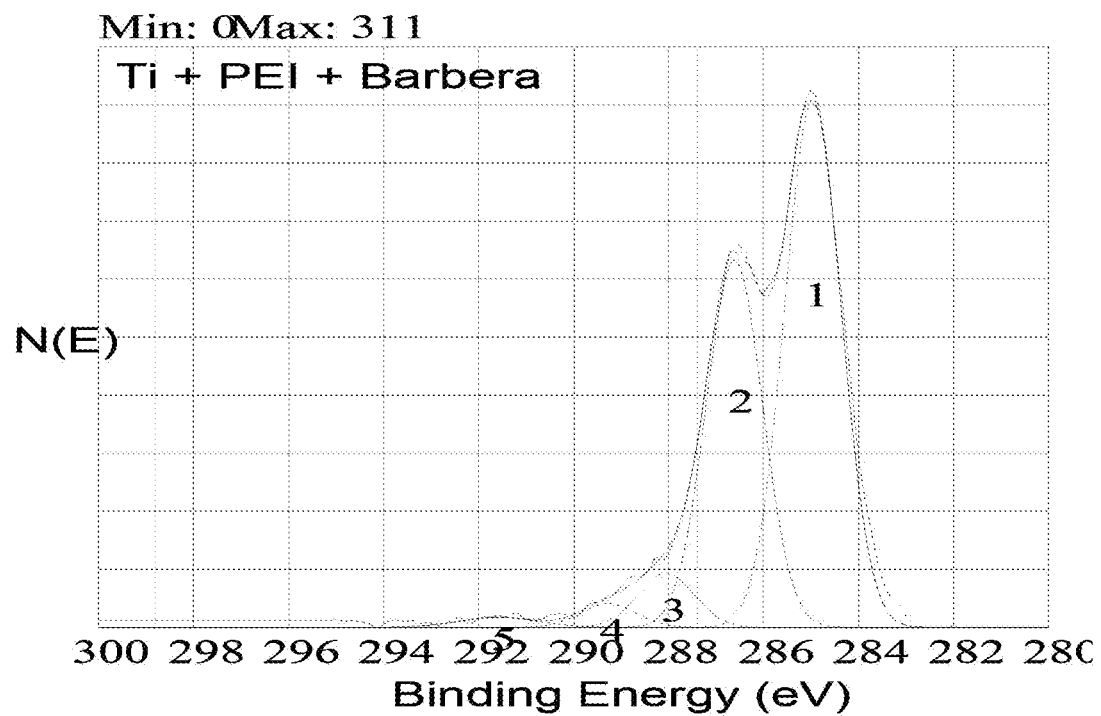
Figure 19:
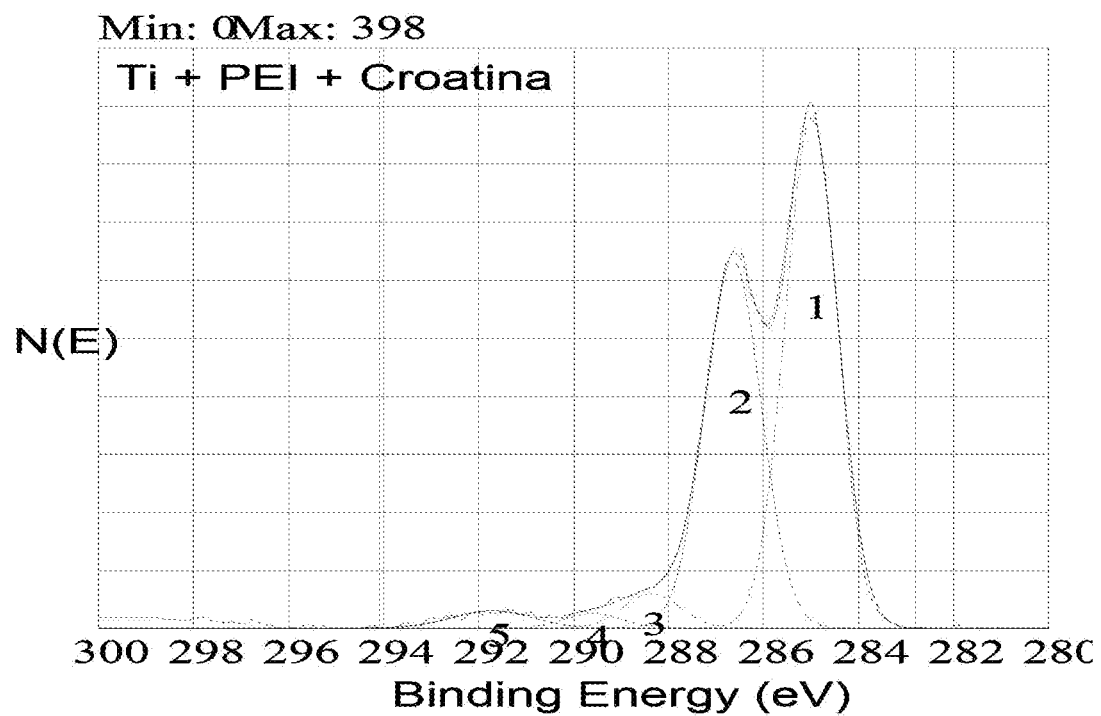
Figure 20:
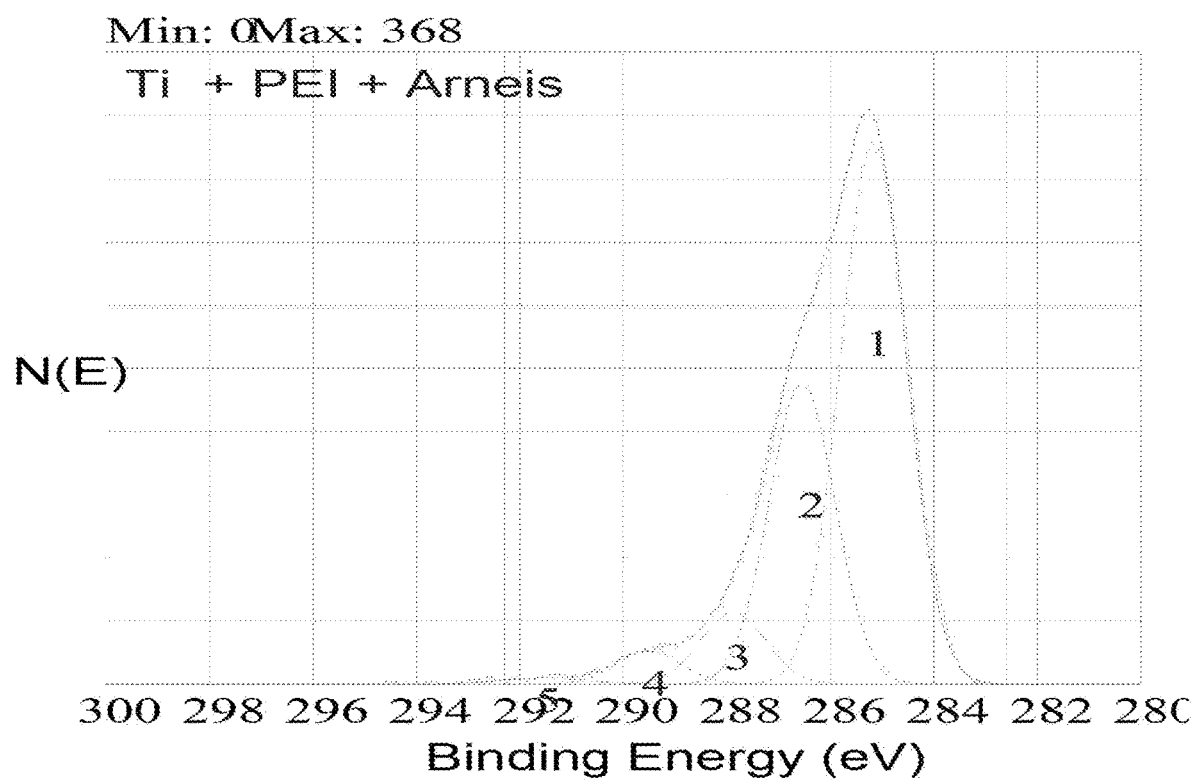

FIG. 16 shows the potential values, showing the following plateau potentials (table 14):

| Grape | Plateau potential (mV) |
|---|---|
| Nebbiolo | −25.1 |
| Barbera | −34.0 |
| Croatina | −38.9 |
| Arneis | −32.8 |

The data indicate that:
the adsorption process, which involves the almost disappearance of the titanium signal, the definition of an organic surface (that is, dominated by the signals of C and O) and the formation of a negative potential plateau in the basic field are a general phenomenon, which takes place with all the compositions evaluated;
the chemical composition of the surface and the absolute value of the plateau potential vary with the variation of the grape, suggesting a different composition of the molecules present on the surface.

These data are in accordance with the general vision of the process, which identifies the surface functionalized with PEI as an "attractor" or "sequestrant" of polyphenolic molecules present in the solution/suspension of extracts, as a function of their abundance and affinity. Starting from extracts with different chemical compositions, the phenomenon happens anyway, although in all probability, molecules at least partially different are selected. From the table of surface chemical composition, the breakdown of the analyzed surfaces in two families is apparent, following what suggested by the composition data of the extracts and, even before, by the visual experience: the three red grapes form a first family (taking the O/C ratio or the absolute value of O or C as indicator), the white grape forms a different family.

To better understand the molecular differences of the obtained surfaces, we used the deconvolution of the peak C1s obtained by XPS, as described above. For each of the samples described, the high-resolution peak C1s was then acquired, operating in the range 280-300 eV with analytical method which provides 200 acquisitions for the optimization of the signal/noise ratio, an acquisition step of 0.1 eV with duration of 50 mS per step.

The peaks obtained were subjected to a best fitting procedure using the instrument software and the following data, taken from the chemical evidence and from the literature:

TABLE 15

| Component | Binding energy (eV) | Functionality |
|---|---|---|
| 1 | 285.0 | C—C, C—H |
| 2 | 286.5 | C—O |
| 3 | 288.0 | C=O |
| 4 | 289.5 | O—C=O |
| 5 | 291.5 | Shake up of aromatic rings |

The shape of the various peaks is assumed to be Gaussian and the best fitting process takes into account the intensity of the band and the FWHM (Full Width at Half Maximum) as main variables, optimizing these values to reproduce the experimental peak.

The results obtained are shown in FIGS. 17-20. In particular, the figures show the four experimentally obtained peaks C1s and the corresponding peaks obtained from the best fitting process, with the optimized components and the sum curve of these components. For each sample, the percentage of area occupied by the various components in the total peak, i.e. the relative abundance of a given functionality, is shown below (table 16):

| | % of occupancy by the components | | | | | |
|---|---|---|---|---|---|---|
| Sample | C—C, C—H | C—O | C=O | O—C=O | Shake up | |
| Ti + PEI + Nebbiolo | 49.6 | 36.1 | 9.0 | 3.8 | 1.5 | |
| Ti + PEI + Croatina | 51.9 | 40.1 | 3.7 | 1.6 | 2.6 | |
| Ti + PEI + Barbera | 53.5 | 37.2 | 5.5 | 2.4 | 1.4 | |
| Ti + PEI + Arneis | 56.7 | 31.5 | 7.5 | 3.4 | 0.9 | |

The data show differences in the chemical neighborhood of the carbon present on the surface of the four samples analyzed. In particular, considering the incidence of the aromatic component, highlighted by the percentage of area occupied by the shakeup peak, it is apparent that it is maximum in the case of extract from "croatina" grape marcs and minimum in that of extract from "arneis" grape marcs. This data is in accordance with the high presence of anthocyanins in the "croatina" grape and of benzoic acids (derivatives of caffeic acid) in the "arneis" grape.

In the context of the surface structures obtained from red grapes and presumably dominated by flavonoids, the "barbera" and "nebbiolo" grapes exhibit a higher incidence of C=O groups than croatina, where C—O bonds are more present, as shown in FIGS. 17-20 and in table 16.

Figure 21:
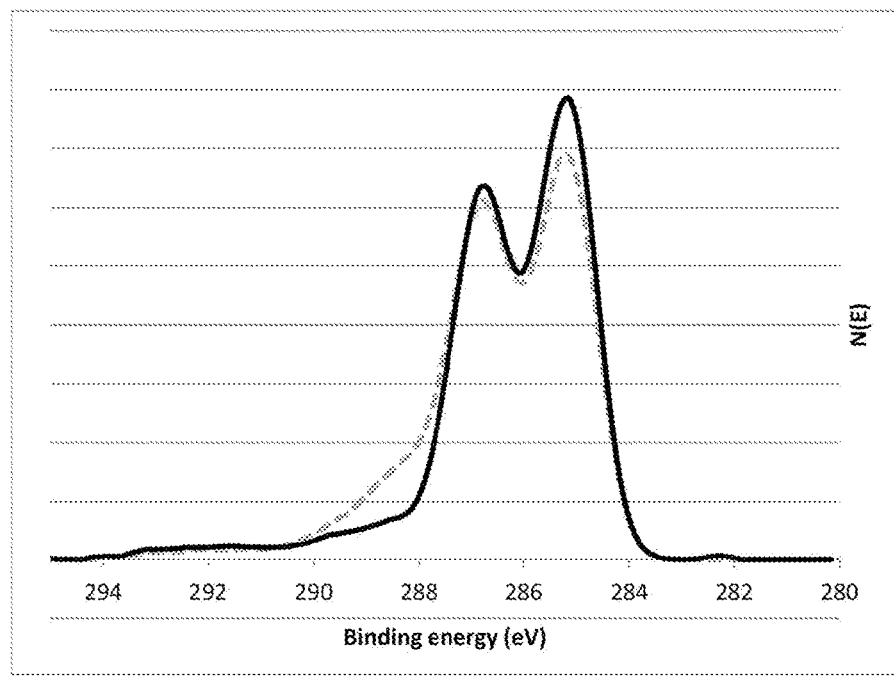
FIG. 21 shows a portion of the XPS spectrum of a Ti+PEI sample+extracts of nebbiolo marcs, before and after treatment with cyanoborohydride.

We conducted a further experiment, consisting in immersing the titanium samples functionalized with "nebbiolo" grape extract in a sodium cyanoborohydride solution at pH 5.5 for two hours and at room temperature. Sodium cyanoborohydride is a reagent used for reductive amination, i.e. for the conversion of labile Schiff bases (C=O+HN— →C=N) into amine bonds (C=N→—C—N—), as also described in WO 2014169959 A1. FIG. 21 shows how the peak C1s of Ti+PEI+Nebbiolo extracts following immersion in sodium cyanoborohydride (dotted line before immersion, continuous line after immersion) varies. There is clearly a noticeable reduction of the "shoulder" at about 288 eV, i.e. the component 3 described above, due to C—O bonds (or C=N bonds, the two components are practically overlapping) which undergo the reductive amination process which originates a covalent bond —C—N—.

This result suggests that:
in the case of coating from "nebbiolo" marcs extracts (but also "barbera", which produces similar results), in which there is a prevailing presence of flavonoids other than anthocyanins, the interaction with the surface occurs to a large extent via the formation of Schiff bases;
for this to happen, the flavonoids present must preferably be those containing a carbonyl group, thus flavanones, flavonols, flavones and flavonones;
differently from what reported using single flavonols, e.g. the quercitrin cited in WO 2014169959 A1, the surface is stable upon release even without specific actions of covalent bond formation and allows the formation of multiple layers (see the data shown above);
the interaction via the formation of Schiff bases is not however the only one present. It has been possible to form multiple layers even in the case of surfaces functionalized with extracts of "arneis" and "croatina" marcs, with evidence of different surface molecular populations, attributable to the composition of the extracts and of the grape.

Biological Effects of Titanium Substrates Functionalized with Extracts from Marcs of Various Grapes The following experiment was conducted:

titanium discs, with a diameter of about 1 cm, were subjected to the surface functionalization process with the extracts of the marcs of the four grapes evaluated above ("nebbiolo", "barbera", "croatina" and "arneis"; using the conventional cell culture methods described above, SaOS2 osteoblastic cells were seeded thereon. In particular, the cells used for the adhesion test are osteoblasts from human osteosarcoma SaOS-2 (BS TCL 90), purchased at the Cell Substrate Center of the Istituto Zooprofilattico Sperimentale of Lombardy and Emilia Romagna. A suspension of $1.05 \pm 0.13 \times 10^5$ SaOS-2/mL (obtained by adding 2 mL of trypsin/EDTA solution to the monolayer within a T75 flask, the density of the cell suspension was calculated using the TC10 Automated Cell Counter instrument, BIO-RAD) in 3 mL of McCoy's 5a medium, supplemented with 15% bovine fetal serum, L-glutamine, penicillin, streptomycin and amphotericin B (all components of the GIBCO cell growth medium come from LIFE TECHNOLOGY Srl, San Giuliano Milanese (MI)) was introduced into a container with 6 sterile wells (6-well multiwell plates, SARSTEDT), containing 4 discs of the same type per well. The operations were performed inside a laminar flow hood FASTER BIO 48 DASIT. The 6-well containers were then withdrawn into an incubator (HERAEUS) at 37° C., 5% $CO_2$ and 98% relative humidity. At the end of each of the 3 experimental times adopted, the discs were removed from the wells, gently washed with phosphate buffer and subjected to the intended tests;

at the established experimental times, four discs were withdrawn by type, two of them were used for cell viability measurements (MTT test described above) and two for measurements of the expression of the genes encoding for two proteins, Osteopontin (OPN) and SPARC (Secreted Protein, Acidic and Rich in Cysteine), both markers of osteoblastic activity. The method used for the evaluation is the real time PCR quantitative analysis technique (qPCR), combined with Inverse Transcription (RT-qPCR). Total RNA was extracted after 72 h, 5 and 7 days of culture, by automated extraction of nucleic acids with the Maxwell RSC Instrument, using Maxwell RSC simplyRNA Cells Kit (Promega). The extracted RNA was then quantified by the Quantus™ Fluorometer (Promega) and the kit associated with it QuantiFluor™ RNA System (Promega). The extracted RNA was then retro-transcribed to obtain the cDNA using the Applied Biosystems High Capacity cDNA Reverse Transcription kit.

The relative quantification of the genes was obtained using Taq Man probes specific for each evaluated gene and GAPDH as reference gene. For each typology of extracts and for unmodified titanium used as reference, two discs per experimental time were used. The amplification was performed using a StepOne Plus thermocycler (Applied Biosystems) according to the manufacturer's instructions. The gene expression graphs were obtained by normalizing the data obtained from the StepOne Plus software analysis, according to the standard $\Delta Ct$ method. The averages obtained from the two discs used for each type and each experimental time were then reported on the gene expression graph.

Figure 22:
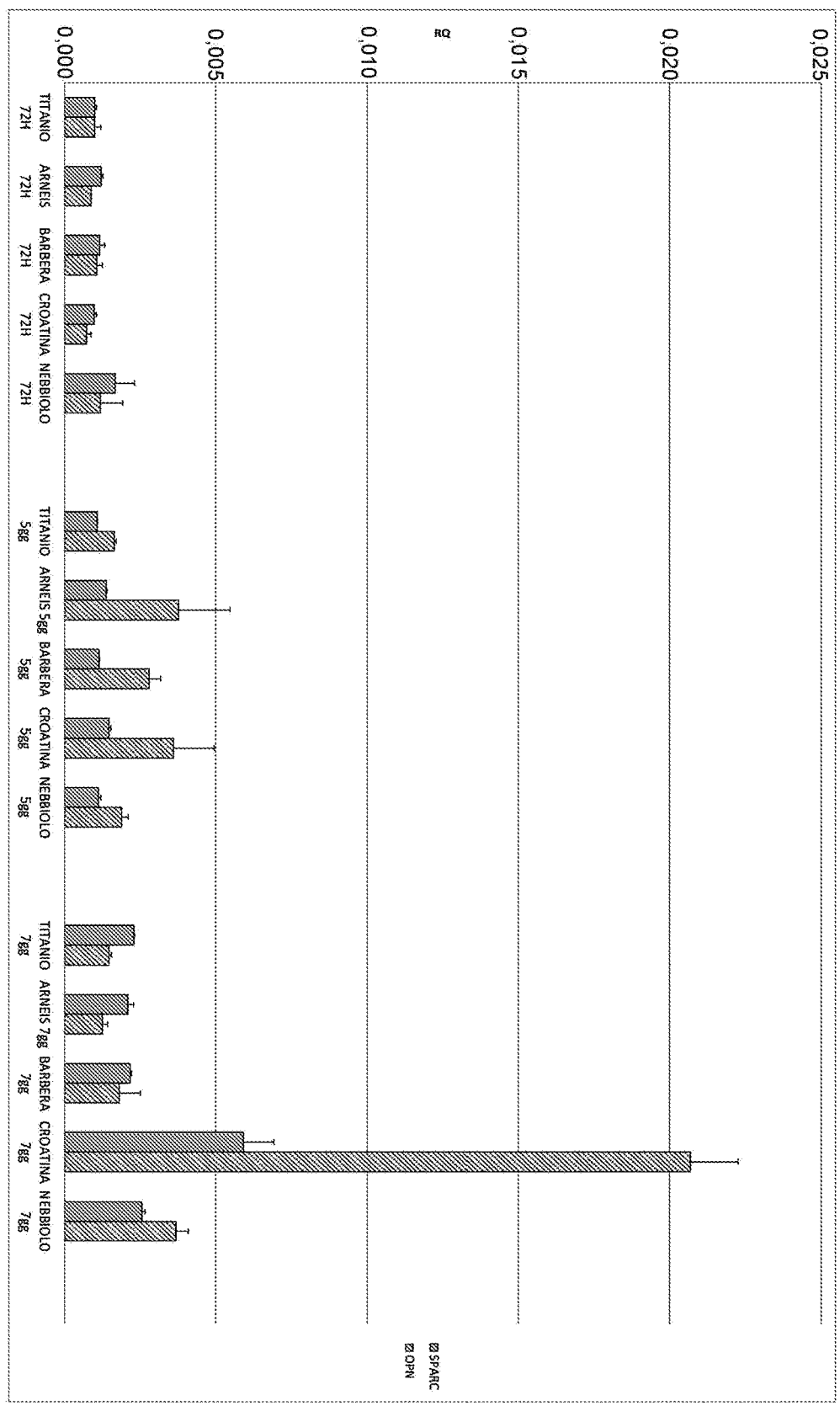
FIG. 22 shows the gene expression of the genes coding for two proteins, Osteopontin (OPN) and SPARC (Secreted Protein, Acidic and Rich in Cysteine) in the samples in FIG. 16.

The data indicated, as regards the MTT test, the progress of the cell surface adhesion and colonization phases with no toxicity effects and significant differences between the samples analyzed. With regard to gene expression evaluations, the results are summarized in FIG. 22.

It is possible to observe that the cells, starting from a situation of substantial equivalence at 72 h, respond to the surface modification with extracts overexpressing the genes indicator of osteogenic activity. In fact, at 5 days the gene encoding for OPN is expressed in greater quantity by the functionalized surfaces. At 7 days, the titanium surface functionalized with extracts of "croatina" marcs has a noticeable overexpression of both markers and also that modified with extracts of "nebbiolo" marcs exhibits an overexpression of a marker.

It is possible to conclude from this experiment that all typologies of surfaces functionalized with extracts enter the cell-material dialogues relative to the expression of the gene encoding for OPN, leading to its overexpression compared to what is observed in the case of titanium alone. In this context, the surface composition obtained by functionalization with extracts of "croatina" marcs, characterized by a higher incidence of aromatic portion resulting from the prevalence of anthocyanins, shows preferential behavior.

Antioxidant Activity of Titanium Substrates Functionalized with Marcs Extracts

Antioxidant activity tests were conducted by applying the DPPH method already described to surface modified titanium discs. The DPPH test allows to determine the antioxidant power by reacting the sample to be analyzed with a solution of DPPH (2,2-diphenyl-1-picrylhydrazyl). The antioxidant compounds are capable of transferring a hydrogen atom to the radical, causing a discoloration of the solution. The decrease of the peak at 525 nm of the DPPH radical is then analyzed with UV-Vis spectrometry after a predetermined incubation time. This discoloration is proportional to the antioxidant charge present in the sample. For the tests with discs, the initial concentration of DPPH was reduced compared to that used in the evaluation of the extracts, the possible reaction being likely to be weak due to the reduced number of molecules on the surface, compared to those present in the extracts, and being substantially an analytical depletion method. For the tests, discs were prepared with PEI monolayer+extracts, with 3 layers (PEI+extracts+PEI+extracts+PEI+extracts) and, similarly, with 6 layers.

The formation and progressive growth of the thickness of the multilayers was immediately evident from the visual appearance: as the surface layer grows, often a few nanometers in the case of monolayers, towards thicknesses comparable to the wavelength of visible light, clearly visible optical interference phenomena are generated. In particular, the following colors were qualitatively observed, the result of a complex interaction between interference phenomena related to the thickness and probably also to absorption phenomena due to the specific composition of the layer:

| Extract: | 1 layer color | 3 layer color | 6 layer color |
| --- | --- | --- | --- |
| Arneis | metal | bronze | bronze |
| Barbera | metal | bronze | bluish-purple |
| Nebbiolo | metal | bronze | bluish |
| Croatina | metal | bronze | bluish-orange |

The presence of polyphenols in the surface layer was confirmed by the XPS analysis, by the methods described above.

Figure 23:
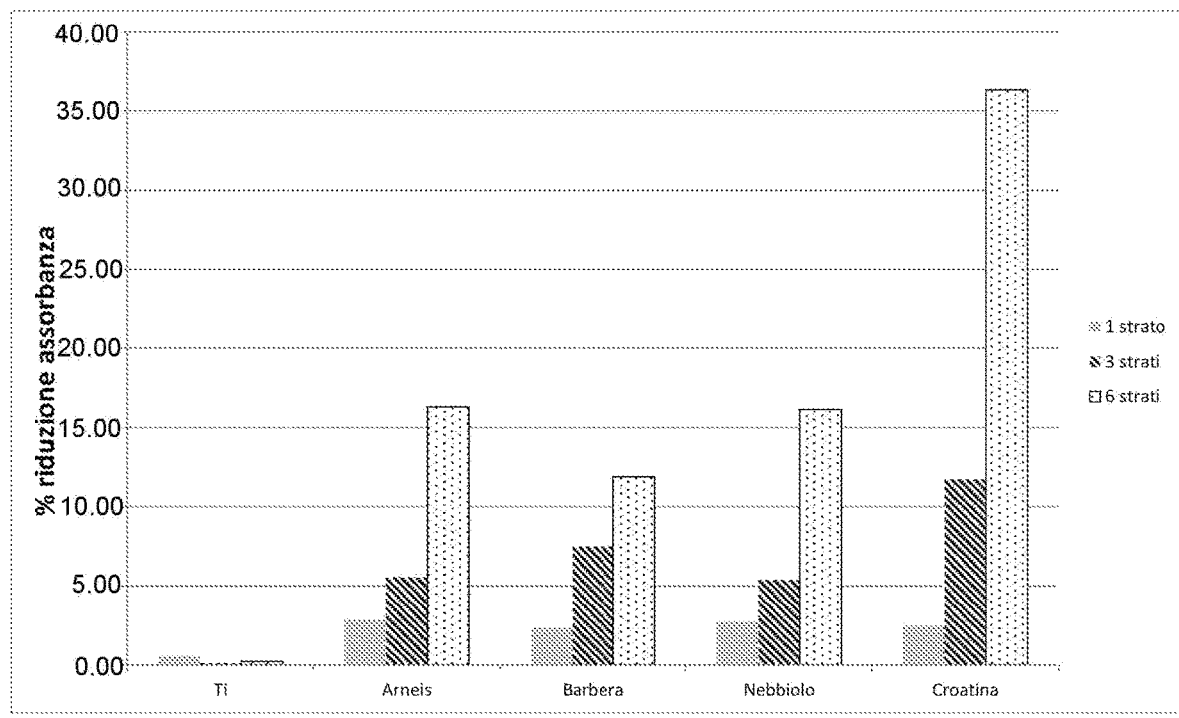
FIG. 23 shows the antioxidant power in the DPPH test (expressed as an absorbance decrease) of the samples in FIG. 16.

The DPPH test was performed by immersing the discs in a tube containing 2 mL of DPPH 0.05 mg/ml solution for 15 minutes in the dark. At the end, the absorbance of the solution was measured and the antioxidant power of the surface was calculated, obtaining the results shown in FIG. 23.

The data confirm the antioxidant power of the surfaces and its increase with the number of layers made, i.e. with the number of polyphenolic molecules available. The data also show that there are quantitative differences between the different extracts, within the framework of a qualitatively common behavior.

It should be noted that the colors described above remained unchanged at the end of the DPPH test, confirming the fact that the surface layer is not altered by the immersion in aqueous solution and that, in other words, no appreciable release of the adsorbed molecules occurs. This behavior was further confirmed by the XPS analysis of the discs subjected to the test, which did not show any titanium signal, an evidence that there was no disintegration of the surface layer and therefore a titanium exposure on the surface.

Figure 24:
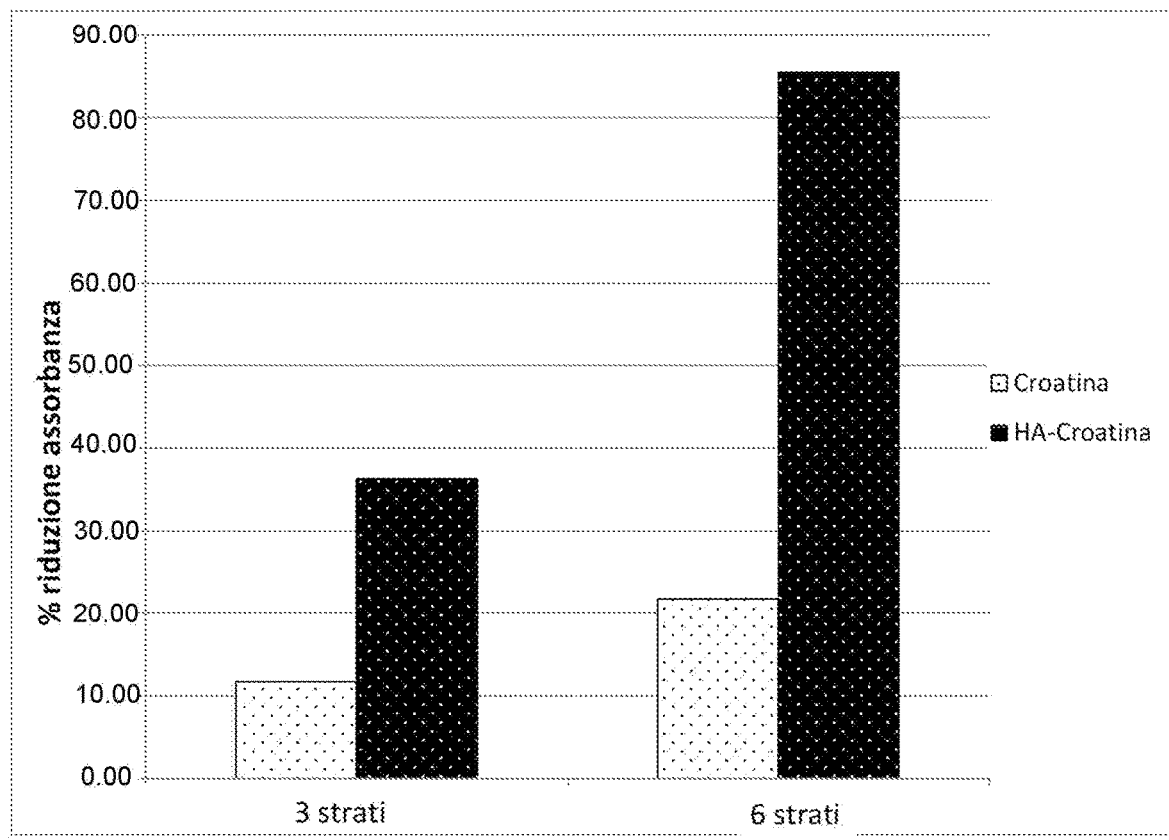
FIG. 24 shows the antioxidant power in the DPPH test (expressed as an absorbance decrease) of a Ti+PEI sample+extracts of croatina marcs+HA in comparison with a Ti+PEI sample+extracts of croatina marcs.

Antioxidant Activity of Titanium Substrates Functionalized by Co-Adsorption of Extracts of Marcs and Hyaluronic Acid 3 and 6 layered discs were prepared by co-adsorption from "croatina" grape extracts and 0.1% HA as described above. The formation of interference stains was observed, also in this case unaltered at the end of the tests in solution. The antioxidant power was evaluated, obtaining the results shown in FIG. 24 (compared with what shown for "croatina" in FIG. 23).

The result is surprising and counter-intuitive. By co-adsorption of HA, obviously, the number of polyphenol molecules present on the surface decreases, since HA itself occupies part of the surface, as shown above. The antioxidant effect, however, is enormously amplified. Without wishing to be limited by any theory, we believe that the presence of HA leads to a more hydrated and more expanded polyphenolic layer structure in aqueous environment, making the surface layers more permeable and therefore increasing the possibility of interaction between polyphenols and DPPH molecules.

In any case, the experimental data indicates that it is possible to provide a titanium disc, and therefore a device made with it, having remarkable antioxidant properties. The same device will also have increased ability to influence the course of cellular colonization in pro-osteogenic direction, as demonstrated by the gene expression data in FIG. 22. As shown above, the presence in the polyphenolic layer of HA at a certain concentration (0.5%) reduces the number of cells present on the surface due to its known cell adhesion resistance features. However, it was shown that by using lower concentrations of HA, the osteogenic effect due to the adsorbed polyphenols was not compromised. Using this evidence, a titanium dental implant was made with the following surface functionalization process:

4 polycation-polyanion PEI+ layer extracts from "croatina" marcs+0.1% HA to amplify the free radical neutralization properties, a fifth layer, the outermost layer, consisting of PEI+ extracts of marcs from "croatina" to exploit the osteogenic properties.

A different titanium dental implant was made with the following surface functionalization process:

4 polycation-polyanion PEI+ layer extracts from "croatina" marcs+0.05% HA to amplify the free radical neutralization properties, a fifth layer, the outermost layer, consisting of PEI+ extracts of marcs from "croatina" to exploit the osteogenic properties.

A different titanium dental implant was made with the following surface functionalization process:

5 polycation-polyanion PEI+ layer extracts from "croatina" marcs+0.01% HA to obtain both the free radical neutralization properties and the osteogenic properties.

Antioxidant Activity after Sterilization of Titanium Substrates Functionalized with Marcs Extracts The surface modification process described above is applied to some dental implants according to the following procedure:

1) dental implants are made with coating with three alternating layers of polyethyleneimine-extracts from Croatina ("extracts" sample);
2) dental implants are made with coating with two alternating layers of polyethyleneimine-extracts from croatina+0.1% hyaluronic acid and a last alternating layer of polyethyleneimine-extract from croatina+0.01% hyaluronic acid ("HA extracts" sample).

Half of the samples thus obtained are stored in the laboratory, the other half is sent to the sterilization process using gamma rays at 25 kGy.

Upon return from sterilization, the antioxidant power of the implants is evaluated according to the DPPH method, as described above.

Figure 25:
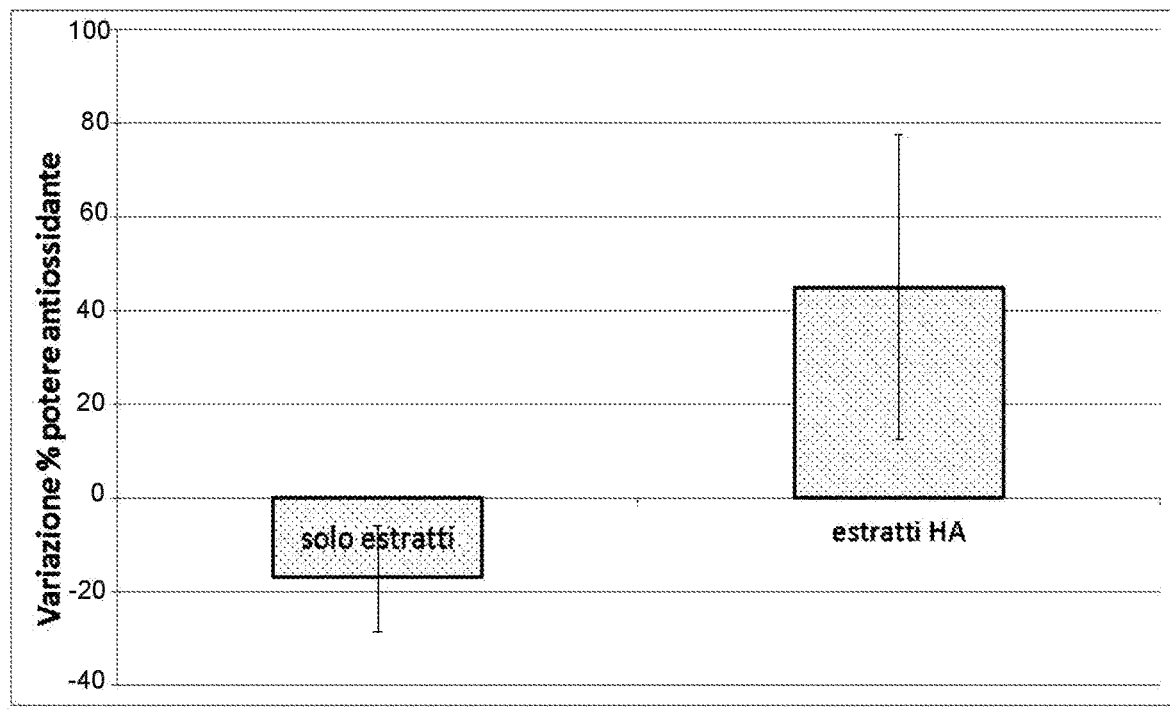
FIG. 25 shows the antioxidant power in the DPPH test of a Ti+PEI sample+extracts of croatina marcs+HA in comparison with a Ti+PEI sample+extracts of croatina marcs after sterilization of the sample.

The results shown in FIG. 25 are obtained, in which the percentage variation of the antioxidant power is shown, setting to 100 the value of the samples not subjected to the sterilization process. In the case of samples made with extracts alone, there is an average decrease of about 16%. In the case of samples made with co-adsorption of HA, an average increase of about 44% is observed. The result is surprising, since damage to the molecular structure by the irradiation, with consequent loss of antioxidant power, is almost predictable but not an increase in the antioxidant activity. Without wishing to be bound to any theory, it can be hypothesized that the effect of irradiation on co-adsorbed layers increases their permeability and availability of antioxidant sites, somehow amplifying the effect induced by the presence of hyaluronic acid.

The invention claimed is:

1. A method for coating a surface of an implant device, wherein said implant device is a titanium bone implant or a titanium dental implant screw and wherein the coating is free of hyaluronic acid, the method comprising, in the following order, the steps of:
   a) treating the surface of the implant device with one or more plasmas selected from the group consisting of: air plasma, oxygen plasma, argon plasma, nitrogen plasma, and other plasmas capable of removing a surface layer of hydrocarbon contamination;
   b) treating the surface of the implant device with an amine substrate;
   c) treating the surface of the implant resulting from step b), by adsorbing a grape marcs extract and drying said functionalized surface;
   d) repeating steps b) and c) at least once, to obtain a substantially homogeneous multilayer coating of grape marcs extract;
   wherein the grape marcs extract is obtained by extraction with an aqueous solution and acetone.

2. The method of claim 1, wherein the amine substrate is polyethyleneimine, in aqueous solution with a concentration ranging from 0.03% to 0.15% in volume based on the total volume of the aqueous solution.

3. The method of claim 1, wherein step c) is conducted at room temperature and for at least 4 hours.

4. The method of claim 1, wherein steps b) and c) are repeated, in consecutive order, 2 to 8 times.

5. The method of claim 1, wherein the marcs is selected from the group consisting of marcs of white grape vines, marcs of red grape vines, marcs with a high rate of anthocyanins and mixtures thereof.

6. The method of claim 5, wherein the marcs is selected from the group consisting of nebbiolo grape, barbera grape, croatina grape, arneis grape and mixtures thereof.

7. The method of claim 1, wherein the grape marcs extracts are mixtures of single-grape marcs extracts.

8. The method of claim 1, further comprising a sterilization step using gamma rays at 25 kGy of the implant treated according to step c).

* * * * *